(12) United States Patent
Kennedy

(10) Patent No.: US 6,706,759 B1
(45) Date of Patent: *Mar. 16, 2004

(54) METHOD OF TREATING CANCER USING DITHIOCARBAMATE DERIVATIVES

(75) Inventor: Thomas Preston Kennedy, Charlotte, NC (US)

(73) Assignee: Charlotte-Mecklenburg Hospital Authority, Charlotte, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/679,932

(22) Filed: Oct. 5, 2000

Related U.S. Application Data

(63) Continuation-in-part of application No. 09/392,122, filed on Sep. 8, 1999, now Pat. No. 6,589,987.
(60) Provisional application No. 60/099,390, filed on Sep. 8, 1998.

(51) Int. Cl.$^7$ ............................................... A61K 31/30
(52) U.S. Cl. ......................................................... 514/499
(58) Field of Search ........................................... 514/499

(56) References Cited

U.S. PATENT DOCUMENTS

| | | | |
|---|---|---|---|
| 4,148,885 A | | 4/1979 | Renoux et al. |
| 4,426,372 A | | 1/1984 | Borch |
| 4,581,224 A | | 4/1986 | Borch |
| 4,594,238 A | | 6/1986 | Borch |
| 4,645,661 A | | 2/1987 | Schonbaum |
| 4,762,705 A | | 8/1988 | Rubin |
| 4,999,347 A | * | 3/1991 | Sorenson ............... 514/499 |
| 5,035,878 A | | 7/1991 | Borch et al. |
| 5,187,193 A | | 2/1993 | Borch et al. |
| 5,380,747 A | | 1/1995 | Medford et al. |
| 5,679,777 A | | 10/1997 | Anderson et al. |
| 5,750,351 A | | 5/1998 | Medford et al. |
| 5,759,517 A | | 6/1998 | Anderson et al. |
| 5,773,209 A | | 6/1998 | Medford et al. |
| 5,773,231 A | | 6/1998 | Medford et al. |
| 5,783,596 A | | 7/1998 | Medford et al. |
| 5,786,344 A | | 7/1998 | Ratain et al. |
| 5,792,787 A | | 8/1998 | Medford et al. |
| 6,156,794 A | | 12/2000 | Faiman et al. |
| 6,548,540 B2 | * | 4/2003 | Kennedy ................ 514/479 |

FOREIGN PATENT DOCUMENTS

| | | |
|---|---|---|
| GB | 2 081 094 A | 2/1982 |
| JP | 4202139 A | 7/1992 |
| WO | WO 99/34763 | 7/1999 |
| WO | WO 99/34784 | 7/1999 |

OTHER PUBLICATIONS

*Protective Effects f Glutathione on Diethyldithiocarbamate (DDC) Cytotoxicity: A Possible Mechanism*, L. D. Trombetta et al., Toxicology and Applied Pharmacology 93, pp. 154–164, 1988.
*Disulfiram and Tumor Inhibition*, H. K. A. Schirmer et al., Transactions of American Association of Genito–Urinary Surgeons, vol. 58, pp. 63–66, 1966.
*Inhibition of Meth–A Tumor Cell Proliferation in Combined Use of Disulfiram with Catalase*, H. Mashiba et al., Toxicology Letters, 61, pp. 75–80, 1992.
*Phase I Study of the Combination of Disulfiram with Cisplatin*, D. J. Stewart et al., Am. J. Clin. Oncol. (CCT), vol. 10, No. 6, pp. 517–519, 1987.
*Antitumor Activity of New Nitrosources on Yoshida Sarcoma Ascites Cells In Vivo*, M. Habs et al., Institute of Toxicology and Chemotherapy, German Cancer Research Center, Heidelberg, FRG, pp. 438–444.
*A Review of the Modulation of Cisplatin Toxicities by Chemoprotectants*, R. T. Dorr, Platinum and Other Metal Coordination Compounds in Cancer Chemotherapy, pp. 131–154, 1996.
*Cytotoxic Interactions of $Zn^{2+}$ In Vitro: Melanoma Cells Are More Susceptible Than Melanocytes*, J. Borovansky et al., Melanoma Research, vol. 7, pp. 449–453, 1997.

* cited by examiner

Primary Examiner—Rebecca Cook
(74) Attorney, Agent, or Firm—Alston & Bird LLP

(57) ABSTRACT

Dithiocarbamate, particularly tetraethylthiuram disulfide, and thiocarbamate anions strongly inhibit the growth of cancer cells of a variety of cell types. Such inhibitory effect is enhanced by heavy metal ions such as copper ions, cytokines and ceruloplasmin. A method is presented for using tetraethylthiuram disulfide to reduce tumor growth, and to potentiate the effect of other anticancer agents.

9 Claims, 16 Drawing Sheets

METHOD OF TREATING CANCER USING DITHIOCARBAMATE DERIVATIVES

CROSS-REFERENCE TO RELATED APPLICATIONS

This application is a continuation-in-part of U.S. patent application Ser. No. 09/392,122, filed on Sep. 8, 1999 now U.S. Pat. No. 6,589,987, which is hereby incorporated herein in its entirety by reference which claims priority under 35 U.S.C. § 119(e) to Provisional U.S. Application Ser. No. 60/099,390, filed Sep. 8, 1998, now abandoned.

FIELD OF INVENTION

This invention generally relates to methods of treating cancer, and particularly to methods of treating cancer using dithiocarbamate derivatives.

BACKGROUND OF THE INVENTION

Cancer, the uncontrolled growth of malignant cells, is a major health problem of the modern medical era and ranks second only to heart disease as a cause of death in the United States. While some malignancies, such as adenocarcinoma of the breast and lymphomas such as Hodgkin's Disease, respond relatively well to current chemotherapeutic antineoplastic drug regimens, other cancers are poorly responsive to chemotherapy, especially non-small cell lung cancer and pancreatic, prostate and colon cancers. Even small cell cancer of the lung, initially chemotherapy sensitive, tends to return after remission, with widespread metastatic spread leading to death of the patient. Thus, better treatment approaches are needed for this illness. Also, because almost all currently available antineoplastic agents have significant toxicities, such as bone marrow suppression, renal dysfunction, stomatitis, enteritis and hair loss.

The end of the twentieth century has seen a more dramatic increase in the observed incidence of malignant melanoma than for all other types of tumors. The biology of malignant melanomas offers an example of the importance of transcription factors for malignant cell propagation. Malignant melanomas have great propensity to metastasize and are notoriously resistant to conventional cancer treatments such as chemotherapy and γ-irradiation. Development of malignant melanoma in humans progresses through a multistage process, with transition from melanocyte to nevi, to radial growth, and subsequently to the vertical growth, metastatic phenotype of autonomous melanomas, associated with decreased dependence on growth factors, diminished anchorage dependence, reduced contact inhibition and increased radiation and drug resistance.

Much of the molecular understanding of melanoma progression has come from studying the response of cultured melanoma cells to mitogenic stimuli. In culture, melanocyte proliferation and differentiation are positively regulated by agents that increase cAMP (See, P. M. Cox, et al., "An ATF/CREB binding motif is required for aberrant constitutive expression of the MHC class II Drα promoter and activation by SV40 T-antigen," *Nucleic Acids Res.* 20:4881–4887 (1992); R. Halaban, et al., "Regulation of tyrosinase in human melanocytes grown in culture," *J. Cell Biol.* 97:480–488 (1983); D. Jean, et al., "CREB and its associated proteins act as survival factors for human melanoma cells," *J. Biol. Chem.* 273:24884–24890 (1998); P. Klatt, et al., "Nitric oxide inhibits c-Jun DNA binding by specifically targeted S-glutathionylation," *J. Biol. Chem.* 274:15857–15864 (1999); J. M. Lehmann, et. al., "MUC18, a marker of tumor progression in human melanoma, shows sequence similarity to the neural cell adhesion molecules of the immunoglobulin superfamily," *Proc. Natl. Acad. Sci. U.S.A.* 89:9891–9895 (1989); M. Luca, et al., "Direct correlation between MUC18 expression and metastatic potential of human melanoma cells," *Melanoma Res.* 3:35–41 (1993); J. P. Richards, et al., "Analysis of the structural properties of cAMP-responsive element-binding protein (CREB) and phosphorylated CREB," *J. Biol. Chem.* 271:13716–13723 (1996); and S. Xie, et al., "Dominant-negative CREB inhibits tumor growth and metastasis of human melanoma cells," *Oncogene* 15:2069–2075 (1997)), and several cAMP responsive transcription factors binding to CRE (the consensus motif 5'-TGACGTCA-3', or cAMP response element) play prominent roles in mediating melanoma growth and metastasis. In MeWo melanoma cells, the transcription factor CREB (for CRE-binding protein) and its associated family member ATF-1 promote tumor growth, metastases and survival through CRE-dependent gene expression. See, D. Jean, et al., supra. Expression of the dominant negative KCREB construct in metastatic MeWo melanoma cells decreases their tumorigenicity and metastatic potential in nude mice. See, S. Xie, et al., "Expression of MCA/MUC18 by human melanoma cells leads to increased tumor growth and metastasis," *Cancer Res.* 57:2295–2303 (1997). The KCREB-transfected cells display a significant decrease in matrix metalloproteinase 2 (MPP2, the 72 kDa collagenase type IV) mRNA and activity, resulting in decreased invasiveness through the basement membrane, an important component of metastatic potential.

The cell surface adhesion molecule MCAM/MUC 18, which is involved in metastasis, of melanoma (See, J. M. Lehmann, et al., supra; M. Luca, et al., supra; S. Xie, et al., supra), is also down-regulated by KCREB transfection. See, S. Xie, et al., *Cancer Res.*, supra. In addition, expression of KCREB in MeWo cells renders them susceptible to thapsigargin-induced apoptosis, suggesting that CREB and its associated proteins act as survival factors for human melanoma cells, thereby contributing to the acquisition of the malignant phenotype. See, D. Jean, et al., supra.

Melanoma cells aberrantly express the major histocompatibility complex class II (MHC II) antigens, normally found only in B-lymphocytes and antigen presenting cells of the monocyte/macrophage cell line. See, P. M. Cox, et al., "An ATF/CREB binding motif is required for aberrant constitutive expression of the MHC class II Drα promoter and activation by SV40 T-antigen. *Nucleic Acids Res.*," 20:4881–4887 (1992). In $B_{16}$ melanoma cells this is due to activation of the MHC II Drα promoter by constitutive activation of an ATF/CREB motif. CREB family proteins also bind to the UV-response element (URE, 5'-TGACAACA-3'), and URE binding of the CREB family member ATF2 confers resistance to irradiation and to the chemotherapeutic drugs cis-platinum, 1-α-D-arabinofuranosylcytosine (araC) or mitomycin C in MeWo melanoma lines. See, Z. Ronai, et al., "ATF2 confers radiation resistance to human melanoma cells," *Oncogene* 16:523–531 (1998)). Thus, CREB family transcription factors play important roles in the malignant potential of this important tumor type. This has led to the suggestion by others that targeted molecular disruption of ATF/CREB-mediated transcription might be therapeutically useful for controlling growth and metastases of relatively treatment-resistant malignant melanoma. See, D. Jean, supra, and Z. Ronai, supra.

The positively charged DNA binding domain of many transcription factors contains cysteines which can be oxidatively modified by agents such as hydrogen peroxide or nitric oxide (NO), stimulating repair processes that result in formation of mixed disulfides between glutathione (GSH) and protein thiols. See, P. Klatt, et al., supra; and, H. Sies, "Glutathione and its role in cellular functions," *Free Rad. Biol. Med.* 27:916–921 (1999)). As a consequence of this so-called protein "S-glutathionylation", the usually positively charged transcription factor DNA binding domain develops an electronegative charge imparted by dual carboxylate end groups of GSH. The change in charge disrupts transcription factor binding to its respective DNA consensus sequence. See, P. Klatt, et al., supra and H. Sies, supra. This mechanism has been demonstrated to explain how NO inhibits c-Jun DNA binding by specifically targeted S-glutathionylation of cysteines within the DNA binding region, and a similar mechanism has been suggested for how nitrosative stress in general might functionally inhibit the activity of Fos, ATF/CREB, Myb and Rel/NFκB family transcription factors. See, P. Klatt, et al., supra.

The dithiocarbamates comprise a broad class of molecules giving them the ability to complex metals and react with sulfhydryl groups and glutathione. After metal-catalyzed conversion to their corresponding disulfides, dithiocarbamates inhibit cysteine proteases by forming mixed disulfides with critical protein thiols. See, C. S. I. Nobel, et al., "Mechanism of dithiocarbamate inhibition of apoptosis: thiol oxidation by dithiocarbamate disulfides directly inhibits processing of the caspase-3 proenzyme," *Chem. Res. Toxicol.* 10:636–643 (1997). CREB contains three cysteines in the DNA binding region ($Cys^{300}$, $Cys^{310}$ and $Cys^{337}$) which are not essential for DNA binding but might provide reactive sites for S-glutathionylation. See, S. Orrenius, et al., "Dithiocarbamtes and the redox regulation of cell death," *Biochem. Soc. Trans.* 24:1032–1038 (1996)).

Recently, dithiocarbamates containing a reduced sulfhydryl group, e.g., pyrrolidinedithiocarbamate (PDTC) have been shown to inhibit the proliferation of cultured colorectal cancer cells. See, Chinery, et al., "Antioxidants enhance the cytotoxicity of chemotherapeutic agents in colorectal cancer: a p53-independent induction of $p21^{WAF1/CIP1}$ via C/EBPβ," *Nature Med.* 3:1233–1241 (1997); Chinery et al., "Antioxidants reduce cyclooxygenase-2 expression, prostaglandin production, and proliferation in colorectal cancer cells." *Cancer Res.* 58:2323–2327 (1998).

In addition to their reduced thioacid form, dithiocarbamates exist in three other forms, e.g., a) the disulfide, a condensed dimmer of the thioacid, with elimination of reduced sulfhydryl groups by disulfide bond formation; b) the negatively charged thiolate anion, generally as the alkali metal salt, such as sodium; and c) the 1,1-dithiolato complexes of the transition elements, in which the two adjoining sulfur atoms of the dithiocarbamate are bound to the same titanium, vanadium, chromium, iron, cobalt, nickel, copper, silver or gold metal ion. The disulfide, thiolate anion and transition metal complexes of dithiocarbamates are all structurally distinct from the reduced form of PDTC used by Chinery, et al., in that they have no reduced sulfhydryl molecular moiety and are incapable of functioning as antioxidants by donating the proton from a reduced sulfhydryl to scavenge electrons of free radical species. Lacking a reduced sulfhydryl, thiocarbamate disulfides, thiolate anions and transition metal complexes should, according to the teachings of Chinery, et al., have no activity as antiproliferative compounds against cancer, since these three nonreduced chemical forms of dithiocarbamates are incapable of functioning as antioxidants.

In U.S. patent application Ser. No. 09/392,122; filed Sep. 8, 1999, it was reported that the dithiocarbamate disulfide disulfiram sensitizes tumor cells to cancer chemotherapy and could be used in conjunction with cancer chemotherapeutic drugs to increase their effectiveness in treating neoplasms. Recently, this effect has been explained in work in which disulfiram was shown to prevent maturation of the P-glycoprotein pump, an ATP-driven 170-kd efflux pump on the plasma membrane that pumps a variety of cytotoxic drugs out of cells. See, T. W. Loo, et al., "Blockage of drug resistance in vitro by disulfiram, a drug used to treat alcoholism." *J. Natl. Cancer Inst.* 92:898–902 (2000). This effect reduces P-glycoprotein-mediated drug resistance in tumor cells and sensitizes tumor cells to cancer chemotherapy.

It is therefore an object of the present invention to provide a method for the treatment of cancer.

Another object of the present invention is to provide pharmaceutical compositions for the treatment of cancer.

It is still another object of the present invention to provide a relatively less toxic agent available for use alone in combination with current drugs in order to better treat cancer patients without risking injury from the therapy itself.

SUMMARY OF THE INVENTION

The present invention provides a method for treating established cancer using dithiocarbamate disulfides, or thiocarbamate anions either alone, or in combination with a heavy metal ion, and thiocarbamate complexes of heavy metal ions.

It has been discovered that dithiocarbamate disulfides and their corresponding thiolate anions alone exhibit potent inhibitory effects on growth of established tumor cells in the absence of antioxidant sulfhydryl groups within their structure. Thiocarbamate disulfides and their corresponding thiolate anions are effective in inhibiting the growth of established melanomas and non-small cell lung cancer cells, which are known to be poorly responsive to currently available neoplastic agents. In addition, it has further been surprisingly discovered that the antiproliferative and antineoplastic effect of dithiocarbamate disulfides and their corresponding thiolate anions on established tumor cells is greatly potentiated by co-treatment of cancer cells with a transitional metal salt in a concentration which by itself does not impair cancer cell growth. The potentiating function of the transition metal is to facilitate formation of the thiolate anion from the dithiocarbamate disulfide. Further the tumor cell growth inhibition effect can be significantly enhanced by the addition of heavy metal ions such as copper, zinc, gold and silver ion, as examples, or by administering the thiocarbamate as a heavy metal ion complex.

The chemical activity of these species is not from antioxidant action but from stimulating formation of mixed disulfides between the dithiocarbamate and sulfhydryl moieties of cysteines located at critical sites on cell proteins, such as the DNA binding region of transcription factors needed to promote expression of gene products necessary for malignant cell proliferation.

Dithiocarbamates disulfides that are useful in the treatment of cancer include, but are not limited to, those of the formulas:

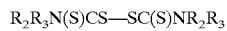

wherein $R_1$, $R_2$, $R_3$ and $R_4$ are the same or different and represent hydrogen, and unsubstituted or substituted alkyl, akenyl, aryl, alkoxy, and heteroaryl groups. It is noted that the alkyl groups can include cycloalky and hetercycloalkyl groups. $R_1$, $R_2$ and the N atom in the formula can together form an N-heterocyclic ring, which is, e.g., heterocycloalkyl or heterocycloaryl. Likewise, $R_3$, $R_1$ and the N atom in the formula can together form an N-heterocyclic ring, which is, e.g., heterocycloalkyl or heterocycloaryl. Typically $R_1$, and $R_2$ are not both hydrogen, and $R_3$ and $R_4$ are not both hydrogen.

In accordance with another aspect of this invention, a method for treating established cancer in a patient is provided comprising administering to the patient a therapeutically effective amount of a dithiocarbamate disulfide, preferably disulfiram, or the corresponding diethyldithiocarbamate thiolate anion, and a heavy metal ion of the formula:

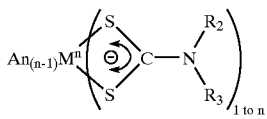

wherein $R_2$ and $R_3$ are the same or different and represent hydrogen, and unsubstituted or substituted alkyl, akenyl, aryl, alkoxy, and heteroaryl groups; An is a metal, e.g., titanium, vanadium, chromium, iron, cobalt, nickel, copper, silver, silver or gold; n is the valence of the metal; and M is sodium, potassium, calcium, magnesium, barium, or lithium or an anion of small molecular weight.

In a preferred embodiment, the heavy metal ion is administered as a complex or chelate with the dithiocarbamate disulfide or corresponding thiolate anion. Suitable heavy metal ions include but are not limited to ions of arsenic, bismuth, cobalt, copper, chromium, gallium, gold, iron, manganese, nickel, silver, titanium, vanadium, selenium, and zinc.

In another preferred embodiment, the dithiocarbamate disulfide or corresponding thiolate anion and the heavy metal ion are administered in combination with another anticancer agent.

In addition, the present invention provides a method for sensitizing cancer cells to chemotherapeutic drugs by the administration of a dithiocarbamate thiolate anion or a dithiocarbamate complex with heavy metals in order to effect inhibition of the tumor cell membrane P-glycoprotein pump which functions to extrude from cancer cells the anti-neoplastic agents which are absorbed.

In accordance with another aspect of the invention, the present invention provides a pharmaceutical composition that comprises a pharmaceutically acceptable carrier, and a complex between a dithiocarbamate and a heavy metal ion. Optionally, the composition can further contain another anticancer agent.

The active compounds of this invention can be administered through a variety of administration routes. For example, they can be administered orally, intravenously, intradermally, subcutaneously and topically.

The present invention is effective for treating various types of cancer, including but not limited to melanoma, non-small cell lung cancer, small cell lung cancer, renal cancer, colorectal cancer, breast cancer, pancreatic cancer, gastric cancer, bladder cancer, ovarian cancer, uterine cancer, lymphoma, and prostate cancer. In particular the present invention will be especially effective in treating melanoma, lung cancer, breast cancer and prostate cancer. Thus the use of dithiocarbamate disulfides and thiolate anions in this invention offers a readily available and easily used treatment for cancers in man and other animals.

DETAILED DESCRIPTION OF THE INVENTION

Figure 1A:
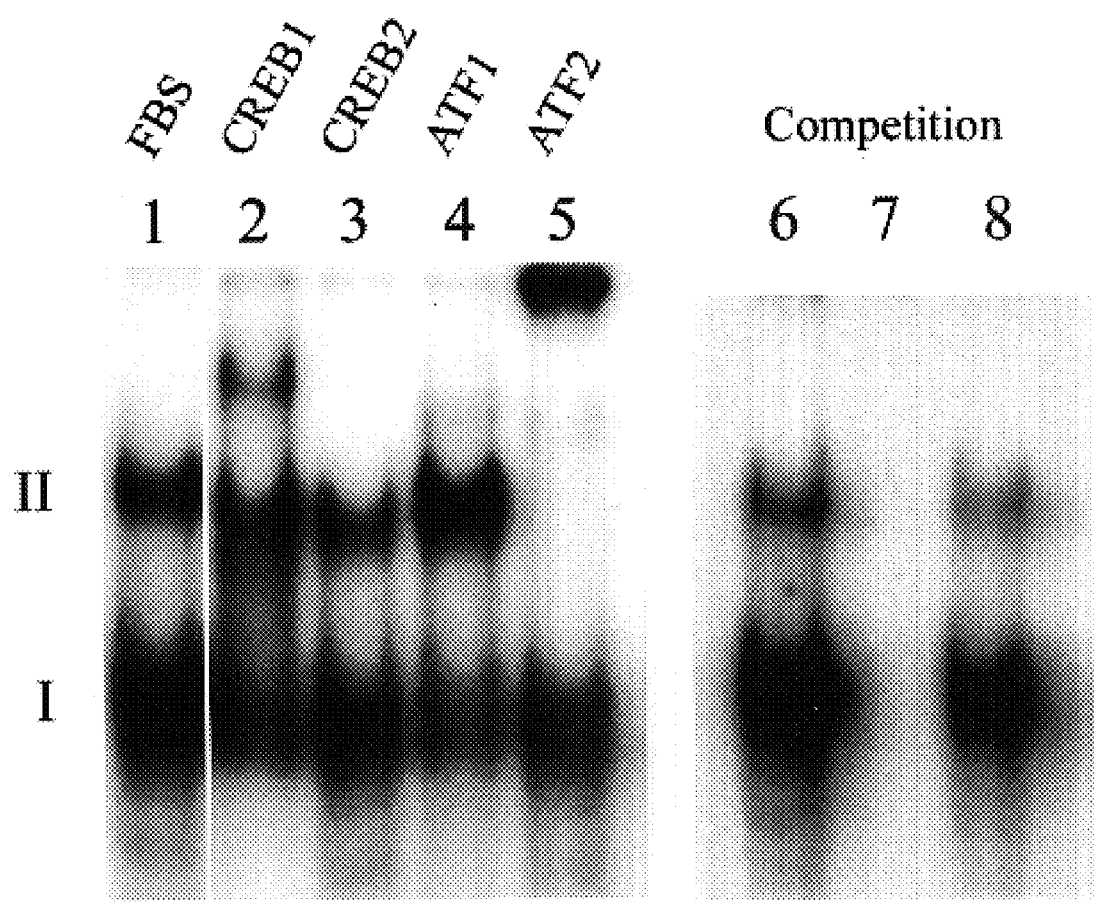
FIG. 1A shows that M1619 melanoma cells exhibit constitutive DNA binding activity to the cyclic AMP response element (CRE);.

The present invention will now be described more fully hereinafter with reference to the accompanying examples, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

As used herein, the term "dithiocarbamate disulfides" refers to compounds having the formula of:

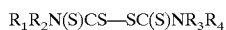

wherein $R_1$, $R_2$, $R_3$ and $R_4$ are the same or different and represent hydrogen, and unsubstituted or substituted alkyl, akenyl, aryl, alkoxy, and heteroaryl groups. It is noted that the alkyl groups can include cycloalky and hetercycloalkyl groups. $R_1$, $R_2$ and the N atom in the formula can together form an N-heterocyclic ring, which is, e.g., heterocycloalkyl or heterocycloaryl. Likewise, $R_3$, $R_4$ and the N atom in the formula can together form an N-heterocyclic ring, which is, e.g., heterocycloalkyl or heterocycloaryl. Typically $R_1$ and $R_2$ are not both hydrogen, and $R_3$ and $R_4$ are not both hydrogen. Thus, dithiocarbamate disulfide is a disulfide form of dithiocarbamates that have a reduced sulfhydryl group.

Many dithiocarbamates are known and synthesized in the art. Non limiting examples of dithiocarbamates include diethyldithiocarbamate, pyrrolodinedithiocarbamate, N-methyl, N-ethyl dithiocarbamates, hexamethylenedithiocarbamate, imidazolinedithiocarbamates, dibenzyldithiocarbamate, dimethylenedithiocarbamate, dipolyldithiocarbamate, dibutyldithiocarbamate, diamyldithiocarbamate, N-methyl, N-cyclopropylmethyldithiocarbamate, cyclohexylamyldithiocarbamate, pentamethylenedithiocarbamate, dihydrxyethyldithiocarbamate, N-methylglucosamine dithiocarbamate, and salts and derivatives thereof Typically, a sulfhydryl-containing dithiocarbamate can be oxidized to form a dithiocarbamate disulfide.

Sulfhydryl-containing dithiocarbamates can be converted to their corresponding thiolate anions by treatment with an alkali-metal hydroxide as a proton acceptor, yielding the structure:

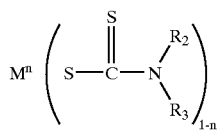
(II B)

wherein $R_2$ land $R_3$ are the same or different and represent hydrogen, and unsubstituted or substituted alkyl, akenyl, aryl, alkoxy, and heteroaryl groups; M is an alkali metal selected from the group consisting of from the group consisting of sodium, potassium, calcium, magnesium, barium, and lithium; and n is the valence of the alkali metal.

Finally, the heavy metal complexes of dithocarbamate can be synthesized either by treatment of the disulfide or the thiolate anion forms of dithiocarbamates with metal salts, yielding a variety of useful metal complexes in which the metal forms a complex with both sulfur atoms:

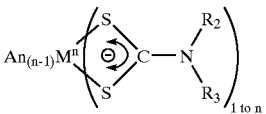

wherein $R_2$ and $R_3$ are the same or different and represent hydrogen, and unsubstituted or substituted alkyl, akenyl, aryl, alkoxy, and heteroaryl groups; An is a metal, e.g., titanium, vanadium, chromium, iron, cobalt, nickel, copper, silver, silver or gold; n is the valence of the metal; and M is sodium, potassium, calcium, magnesium, barium, or lithium or an anion of small molecular weight.

Specifically, the preferred gold 1,1-dithio chelates of dithiocarbamates has the formulae:

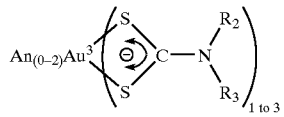

wherein $R_2$, $R_3$ are ethyl, and An is an anion of small molecular weight.

Any pharmaceutically acceptable form of dithiocarbamate disulfides, their corresponding thiolate anions and dithiocarbamate metal chelates can be used. For example, tetraethylthiuram disulfide, which is known as disulfiram, is used in one embodiment of this invention. Disulfiram has the following formula:

where $R_1$, $R_2$, $R_3$ and $R_4$ are all ethyl. Disulfiram has been used clinically in the treatment of alcohol abuse, in which disulfiram inhibits hepatic aldehyde dehydrogenase.

The thiolate anion derivative of disulfiram is diethyldithiocarbamate anion, the sodium salt of which has the following formula:

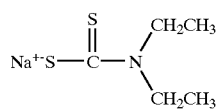

Finally, the heavy metal complex of diethyldithiocarbamate, exemplified below as the gold (Au III) 1,1-dithiolato complex, is shown:

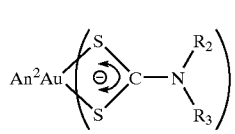
(II C)

wherein $R_2$ and $R_3$ are ethyl, and An is an anion of small molecular weight.

Methods of making dithiocarbamates and their disulfides are generally known in the art. Exemplary methods are disclosed in, e.g., Thorn, et al, *The Dithiocarbamates and Related Compounds*, Elsevier, N.Y., 1962; and U.S. Pat. Nos. 5,166,387, 4,144,272; 4,066,697, 1,782,111, and 1,796,977, all of which are incorporated herein by reference.

The term "treating cancer" as used herein, specifically refers to administering therapeutic agents to a patient diagnosed of cancer, i.e., having established cancer in the patient, to inhibit the further growth or spread of the malignant cells in the cancerous tissue/ and/or to cause the death of malignant cells.

This invention provides a method for treating cancer in a patient. In accordance with the present invention, it has been discovered that dithiocarbamate disulfides, their corresponding thiolate anions, and their heavy metal complexes, such as disulfiram, the diethyldithiocarbamate anion and dichloro(ditheylthiocarbamyl)gold (II), respectively, can inhibit the growth of tumor cells in a heavy metal ion-dependent manner. Specifically, heavy metal ions such as copper, zinc, gold, and silver ions significantly enhance the inhibitory effect of dithiocarbamate disulfides and their thiolate anions on tumor cells, while depletion of such heavy metal ions prevents growth inhibition by disulfiram and the diethyldithiocarbamate anion. The function performed by the metal is to chemically catalyze formation of or stabilize the thiolate anion form in vivo, so that the thiolate anion is able to form mixed disulfides with protein cysteine sulfhydryl groups of cellular proteins.

In accordance with one aspect of this invention, a method for treating an established cancer in a patient is provided. A dithiocarbamate disulfide can be administered to a patient having established cancer to treat the cancer. Preferably, the thiuram disulfide administered is a tetra alkyl thiuram disulfide such as teraethylthiuram disulfide, i.e., disulfiram.

In another aspect of the invention, the method for treating cancer in a patient comprises administering to the patient a therapeutically effective amount of a dithiocarbamate thiolate anion.

In another aspect of the invention, the method for treating cancer in a patient comprises administering to the patient a therapeutically effective amount of a dithiocarbamate disulfide or its thiolate anion, and a heavy metal ion.

Non-limiting examples of heavy metal ions include ions of arsenic, bismuth, cobalt, copper chromium, gallium, gold iron, manganese, nickel, silver, titanium, vanadium, selenium and zinc. Preferably, gold, silver, zinc, selenium, and copper ions are used. Sources of such heavy metal ions are known to the those skilled in the art. For example, such ions can be provided in a sulfate salt, or chloride salt form, or any other pharmaceutically suitable forms. Preferably, the salt is in a chelated form, complexed with a pharmaceutically acceptable organic anion such as acetate, glycinate, gluconate, propionate or lactate so that absorption of the metal from the gastrointestinal tract is enhanced.

One or more dithiocarbamate disulfide or corresponding thiolate anions and one or more heavy metal ions can be administered to the patient. The dithiocarbamate disulfide or thiolate anion and the heavy metal ion can be administered in combination or separately. Preferably, they are administered as a chelating complex. As is known in the art, dithiocarbamates are excellent chelating agents and can chelate heavy metal ions to form chelates. Preparation of chelates of dithiocarbamates and heavy metal ions are known to the ordinary artisan. For example, chelates of diethyldithiocarbamate and copper, zinc, silver, or gold ions can be conveniently synthesized by mixing, in suitable solvents, disulfiram or sodium diethyldithiocarbamate with, e.g., $CuSO_4$, $ZnCl_2$, $C_3H_5AgO_3$, or $HAuCl_4.3H_2O$ to allow chelates to be formed. Other dithiocarbamate-heavy metal ion chelates are disclosed in, e.g., D. Coucouvanis, "The chemistry of the dithioacid and 1,1-dithiolate complexes," Prog. Inorganic Chem. 11:234–371 (1970); D. Coucouvanis, "The chemistry of the dithioacid and 1,1-dithiolate complexes, 1968–1977," Prog. Inorganic Chem. 26:302–469 (1978); R. P. Burns, et al., "1,1-ithiolato complexes of the transition metals," Adv. Inorganic Chem. and Radiochem. 23:211–280(1980); L. I. Victoriano, et al., "The reaction of copper (II) chloride and tetralkythiuram disulfides," J. Coord. Chem. 35:27–34 (1995); L. I. Victoriano, et al., "Cuprous dithiocarbamates. Syntheses and reactivity," J. Coord. Chem. 39:231–239 (1996), which are incorporated herein by reference.

In accordance with another aspect of this invention, a method for treating cancer in a patient is provided which includes administering to the patient a therapeutically effect amount of a dithiocarbamate anion compound and an intracellular heavy metal ion stimulant, which can enhance the intracellular level of the above described heavy metal ions in the patient.

Intracellular heavy metal ion carriers are known. For example, ceruloplasmin can be administered to the patient to enhance the intracellular copper level. Other heavy metal ion carriers known in the art may also be administered in accordance with this aspect of the invention. The heavy metal ion carriers and the dithocarbamate disulfide or thiolate anion can be administered together or separately, and preferably in separate compositions.

Ceruloplasmin is a protein naturally produced by the human body and can be purified from human serum. This 132-kD glycoprotein, which carries 7 copper atoms complexed over three 43–45 kD domains, is an acute phase reactant and the major copper-carrying protein in human plasma. See, Halliwell, et al., Methods Enzymol. 186:1–85 (1990). When transported into cells, at least some of the bound cupric ions can be accessible for complexation with the dithiocarbamate disulfide or thiolate anion administered to the patient. See, Percival, et al., Am. J. Physiol. 258:3140–3146 (1990). Ceruloplasmin and dithiocarbamate disulfides or thiolate anions are typically administered in different compositions. Dithiocarbamate disulfides or thiolate anions can be administered at about the same time, or at some time apart. For example, ceruloplasmin can be administered from about five minutes to about 12 hours before or after dithiocarbamate disulfide or thiolate anions are administered to the patient.

In another embodiment, instead of heavy metal ion carriers, a cytokine is administered to the patient in addition to a dithiocarbamate disulfide or corresponding thiolate anion. Suitable cytokines include, e.g., interferon α, interferon β, interferon γ, and interleukin 6 (IL-6). Such cytokines, when administered to a patient, are capable of inducing an acute phase response in the body of the patient, thus stimulating elevations of serum ceruloplasmin in the patient.

The biochemical and physiological properties of such cytokines have been studied extensively in the art and are familiar to skilled artisans. The cytokines can be purified from human or animal serum. They can also be obtained by genetic engineering techniques. In addition, commercially available samples of the above-identified cytokines may also be used in this invention. Genetically or chemically modified cytokines can also be administered. For example, it is known that certain peptide cytokines have longer circulation time in animals when such cytokines are conjugated with a water soluble, non-immunogenic polymer such as polyethylene glycol.

Typically, the cytokines are administered in a different composition from the dithiocarbamate disulfide or corresponding thiolate anion. The cytokines and dithocarbamate disulfide or thiolate anion can be administered at about the same time, or at some time apart from each other. For example the cytokines can be administered from about 5 minutes to about 24 hours before or after the administration of dithiocarbamate disulfide or thiolate anion.

In accordance with another aspect of this invention, the method of this invention can be used in combination with a conventional cancer chemotherapy, with the result that the treatment with dithiocarbamate disulfides or thiolate anions, with or without heavy metals separately or as dithocarbamate-heavy metal chelates, will increase the sensitivity of the tumor to conventional cancer chemotherapy and result in greater effectiveness of the conventional cancer chemotherapy drug. For example, the method of this invention can be complemented by a conventional radiation therapy or chemotherapy. Thus, in one embodiment of this invention, the method of this invention comprises administering to a patient a dithiocarbamate disulfide compound or corresponding thiolate anion and heavy metals, and another anticancer agent. Treatment by ceruloplasmin or a cytokine, and a dithiocarbamate disulfide or thiolate anion can also be conducted along with the treatment with another anticancer agent to increase the effectiveness of the anticancer agent.

Any anticancer agents known in the art can be used in this invention so long as it is pharmaceutically compatible with the dithiocarbamate disulfide or thiolate anion compound, heavy metal ion, ceruloplasmin, and/or cytokines used. By "pharmaceutically compatible" it is intended that the other anticancer agent will not interact or react with the above composition, directly or indirectly, in such a way as to adversely affect the effect of the treatment of cancer, or to cause any significant adverse side reaction in the patient.

Exemplary anticancer agents known in the art include busulphan, chlorambucil, hydroxyurea, ifosfamide, mitomycin, mitotane, chlorambucil, mechlorethamine, carmustine, lomustine, cisplatin, carmustine, herceptin, carboplatin, cyclophosphamide, nitrosoureas, fotemustine, vindescine, etoposide, daunorubicin, adriamycin, paclitaxel, docetaxel, streptozocin, dactinomycin, doxorubicin, idarubicin, plicamycin, pentostatin, mitotoxantrone, valrubicin, cytarabine, fludarabine, floxuridine, clardribine, methotrexate, mercaptopurine, thioguanine, capecitabine, irinotecan, dacarbazine, asparaginase, gemcitabine, altretamine, topotecan, procarbazine, vinorelbine, pegaspargase, vincristine, rituxan, vinblastine, tretinoin, teniposide, fluorouracil, melphalan, bleomycin, salicylates, aspirin, piroxicam, ibuprofen, indomethacin, naprosyn, diclofenac, tolmetin, ketoprofen, nambuetone, oxaprozin, doxirubicin, nonselective cycclooxygenase inhibitors such as nonsteroidal anti-inflammatory agents (NSAIDS), and selective cyclooxygenase-2 (COX-2) inhibitors.

The anticancer agent used can be administered simultaneously in the same pharmaceutical preparation with the dithiocarbamate disulfide or thiolate anion compound, heavy metal compounds or dithiocarbamate-heavy metal chelates, ceruloplasmin, and/or cytokines as described above. The anticancer agent can also be administered at about the same time but by a separate administration. Alternatively, the anticancer agent can be administered at a different time from the administration of the dithiocarbamate disulfide or thiolate anion compound, heavy metal compounds or dithiocarbamate-heavy metal chelates, ceruloplasmin, and/or cytokines. Some minor degree of experimentation may be required to determine the best manner of administration, this being well within the capability of one-skilled in the art once apprised of the present disclosure.

The methods of this invention a particularly useful in treating humans. Also, the methods of this invention are suitable for treating cancers in animals, especially mammals such as canine, bovine, porcine, and other animals. The methods are useful for treating various types of cancer, including but not limited to melanoma, non-small cell lung cancer, small cell lung cancer, renal cancer, colorectal cancer, breast cancer, pancreatic cancer, gastric cancer, bladder cancer, ovarian cancer, uterine cancer, lymphoma, and prostate cancer. In particular, the present invention will be especially effective in treating melanoma, lung cancer, breast cancer, and prostate carcinoma.

The active compounds of this invention are typically administered in a pharmaceutically acceptable carrier through any appropriate routes such as parenteral, intravenous, oral, intradermal, subcutaneous, or topical administration. The active compounds of this invention are administered at a therapeutically effective amount to achieve the desired therapeutic effect without causing any serious adverse effects in the patient treated.

The dithiocarbamate disulfide compound disulfiram and its diethyldithiocarbamate thiolate anion are effective when administered at amounts within the conventional clinical ranges determined in the art. Disulfiram approved by the U.S. Food and Drug administration (Antabuse®) can be purchased in 250 and 500 mg tablets for oral administration from Wyeth-Ayerst Laboratories in Philadelphia, Pa. 19101. Typically, it is effective at an amount of from about 125 to about 1000 mg per day, preferably from 250 to about 500 mg per day for disulfiram and 100 to 500 mg per day or 5 mg/kg in travenously or 10 mg/kg orally once a week for diethyldithiocarbamate. However, the dosage can vary with the body weight of the patient treated. The active ingredient may be administered at once, or may be divided into a number of smaller doses to be administered at predetermined intervals of time. The suitable dosage unit for each administration of disulfiram is, e.g., from about 50 to about 1000 mg/day, preferably from about 1250 to about 500 mg/day. The desirable peak concentration of disulfiram generally is about 0.05 to about 10 $\mu$M, preferably about 0.5 to about 5 $\mu$M, in order to achieve a detectable therapeutic effect. Similar concentration ranges are desirable for dithiocarbamate thiolate anions and for dithocarbamate-heavy metal complexes.

Disulfiram implanted subcutaneously for sustained release has also been shown to effective at an amount of 800 to 1600 mg to achieve a suitable plasma concentration. This can be accomplished by using aseptic techniques to surgically implant disulfiram into the subcutaneous space of the anterior abdominal wall. See, e.g., Wilson, et al., *J. Clin. Psych.* 45:242–247 (1984). In addition, sustained release dosage formulations, such as an 80% poly(glycolic-co-L-lactic acid) and 20% disulfiram, may be used. The therapeutically effective amount for other dithiocarbamate disulfide compounds may also be estimated or calculated based on the above dosage ranges of disulfiram and the molecular weights of disulfiram and the other dithiocarbamate disulfide compound, or by other methods known in the art.

The diethyldithiocarbamate thiolate anion has not been previously advocated as a cancer chemotherapeutic agent itself, nor has it been suggested as a treatment to increase the sensitivity of tumors to cancer chemotherapy drugs. For the treatment of HIV infection, humans have been treated with doses of 5 mg/kg intravenous or 10 mg/kg orally, once a week. Minimal side effects on this dosage regimen include a metallic taste in the mouth, flatulence and intolerance to alcoholic beverages. An enteric-coated oral dosage form of diethyldithiocarbamate thiolate anions to liberate active drug only in the alkaline environment of the intestine is preferred because of the potential for liberation of carbon disulfide upon exposure of diethyldithiocarbamate to hydrochloric acid in the stomach. An oral enteric-coated form of sodium diethyldithiocarbamate is available in 125 mg tablets as Imuthiol® through Institute Merieux, Lyon, France.

Heavy metal ions can be administered separately as an aqueous solution in a pharmaceutically suitable salt form. The salt form is ideally a chelate with an organic anion such as acetate, lactonate, glycinate, citrate, propionate or gluconate in order to enhance absorption. However, the heavy metals are preferably administered in a chelate form in which the ions are complexed with the dithiocarbamate as a 1,1-dithiolate complex. Thus, the amount of heavy metal ions to be used advantageously is proportional to the amount of dithiocarbamate disulfide compound to be administered based on the molar ratio between a heavy metal ion and the dithiocarbamate in the chelate. Methods for preparing such chelates or complexes are known and the preferred methods are disclosed above and in the examples below.

The therapeutically effective amount of IL-6 can be from about 1 to about 100 $\mu$g/kg per day, preferably from about 5 to about 50 $\mu$g/kg per day. Interferon $\alpha$ can be administered at from about $0.1 \times 10^6$ to about $10 \times 10^6$ international units per day, preferably from about 3 to about $8 \times 10^6$ international units per day, and the administration frequency can be from about three times per week to about once per day. Suitable dosage for interferon $\beta$ can range from about 1 to about 200 $\mu$g per day, preferably from about 10 to about 100 $\mu$g per day administered once per week up to once per day. Interferon $\gamma$ can be administered at a dosage of from about 1 to about 1000 $\mu$g per day, preferably from about 50 to about 250 $\mu$g per day. Ceruloplasmin may be administered at an amount of from about 1 to about 100 mg per day, preferably from about 50 to about 30 mg per day.

It should be understood that the dosage ranges set forth above are exemplary only and are not intended to limit the scope of this invention. The therapeutically effective amount for each active compound can vary with factors including but not limited to the activity of the compound used, stability of the active compound in the patient's body, the severity of the conditions to be alleviated, the total weight of the patient treated, the route of administration, the ease of absorption, distribution, and excretion of the active compound by the body, the age and sensitivity of the patient to be treated, and the like, as will be apparent to a skilled artisan. The amount of administration can also be adjusted as the various factors change over time.

Advantageously, the active compounds are delivered to the patient parenterally, i.e., intravenously or intramuscularly. For parenteral administration, the active compounds can be formulated into solutions or suspensions, or in lyophilized forms for conversion into solutions or suspensions before use. Sterile water, physiological saline, e.g., phosphate buffered saline (PBS) can be used conveniently as the pharmaceutically acceptable carriers or diluents. Conventional solvents, surfactants, stabilizers, pH balancing buffers, anti-bacteria agents, and antioxidants can all be used in the parenteral formulations, including but not limited to acetates, citrates or phosphate buffers, sodium chloride, dextrose, fixed oils, glycerine, polyethylene glycol, propylene glycol, benzyl alcohol, methyl parabens, ascorbic, acid, sodium bisulfite, and the like. For parenteral administration, the active compounds, particularly dithiocarbamate-metal chelates, can be formulated contained in liposomes so as to enhance absorption and decrease potential toxicity. The parenteral formulation can be stored in any conventional containers such as vials, ampoules, and syringes.

The active compounds can also be delivered orally in enclosed gelatin capsules or compressed tablets. Capsules and tablets can be prepared in any conventional techniques. For example, the active compounds can be incorporated into a formulation which includes pharmaceutically acceptable carriers such as excipients (e.g., starch, lactose), binders (e.g., gelatin, cellulose, gum), disintegrating agents (e.g., alginate, Primogel, and corn starch), lubricants (e.g., magnesium stearate, silicon dioxide), and sweetening or flavoring agents (e.g., glucose, sucrose, saccharin, methyl salicylate, and peppermint). Various coatings can also be prepared for the capsules and tablets to modify the flavors, tastes, colors, and shapes of the capsules and tablets. In addition, liquid carriers such as fatty oil can also be included in capsules. For administration of dithiocarbamate thiolate anions and dithiocarbamate-metal complexes, it is desirable to administer the compounds as enteric-coated capsules that are impervious to stomach acid but dissolve in the alkaline environment of the small intestine, in order to prevent release of carbon disulfide from dithiocarbamates in the acid environment of the stomach, and to preserve the integrity of the dithiocarbamate-metal chelate.

Other forms of oral formulations such as chewing gum, suspension, syrup, wafer, elixir, and the like can also be prepared containing the active compounds used in this invention. Various modifying agents for flavors, tastes, colors, and shapes of the special forms can also be included. In addition, for convenient administration by enteral feeding tube in patients unable to swallow, the active compounds can be dissolved in an acceptable lipophilic vegetable oil vehicle, such as olive oil, corn oil, and safflower oil.

The active compounds can also be administered topically through rectal, vaginal, nasal or mucosal applications. Topical formulations are generally known in the art including creams, gels, ointments, lotions, powders, pastes, suspensions, sprays, and aerosols. Typically, topical formulations include one or more thickening agents, humectants, an/or emollients including but not limited to xanthan gum, petrolatum, beeswax, or polyethylene glycol, sorbitol, mineral oil, lanolin, squalene, and the like. A special form of topical administration is delivery by a transdermal patch. Methods for preparing transdermal patches are disclosed, e.g., in Brown, et al., *Annual Review of Medicine.* 39:221–229 (1988), which is incorporated herein by reference.

The active compounds can also be delivered by subcutaneous implantation for sustained release. This may be accomplished by using aseptic techniques to surgically implant the active compounds in any suitable formulation into the subcutaneous space of the anterior abdominal wall. See, e.g., Wilson, et al., *J. Clin. Psych.* 45:242–247 (1984). Sustained release can be achieved by incorporating the active ingredients into a special carrier such as a hydrogel. Typically, a hydrogel is a network of high molecular weight biocompatible polymers, which can swell in water to form a gel like material. Hydrogels are generally known in the art. For example, hydrogels made of polyethylene glycols, or collage, or poly(glycolic-co-L-lactic acid) are suitable for this invention. See, e.g., Phillips, et. al., *J. Pharmceut. Sci.* 73:1718–1720 (1984).

The active compounds can also be conjugated, i.e., covalently linked, to a water soluble non-immunogenic high molecular weight polymer to form a polymer conjugate. Advantageously, such polymers, e.g., polyethylene glycol, can impart solubility, stability, and reduced immunogenicity to the active compounds. As a result, the active compound in the conjugate when administered to a patient, can have a longer half-life in the body, and exhibit better efficacy. PEGylated proteins are currently being used in protein replacement therapies and for other therapeutic uses. For example, PEGylated adenosine deaminase. (ADAGEN®) is being used to treat severe combined immunodeficiency disease (SCIDS). PEGylated L-asparaginase (ONCAPSPAR®) is being used to treat acute lymphoblastic leukemia (ALL).

Alternatively, other forms of controlled release or protection including microcapsules and nanocapsules generally known in the art, and hydrogels described above can all be utilized in oral, parenteral, topical, and subcutaneous administration of the active compounds.

As discussed above, another preferable delivery form is using liposomes as a carrier. Liposomes are micelles formed from various lipids such as cholesterol, phospholipids, fatty acids and derivatives thereof. Active compounds can be enclosed within such micelles. Methods for preparing liposomal suspensions containing active ingredients therein are generally known in the art and are disclosed in, e.g., U.S. Pat. No. 4,522,811, which is incorporated herein by reference. Several anticancer drugs delivered in the form of liposomes are known in the art and are commercially available from Liposome, Inc., of Princeton, N.J. It has been shown that liposomal delivery can reduce the toxicity of the active compounds, and increase their stability.

The active compounds can also be administered in combination with other active agents that treat or prevent another disease or symptom in the patient treated. However, it is to be understood that such other active agents should not interfere with or adversely affect the effects of the active compounds of this invention on the cancer being treated. Such other active agents include but are not limited to antiviral agents, antibiotics, antifungal agents, anti-inflammation agents, antithrombotic agents, cardiovascular drugs, cholesterol lowering agents, hypertension drugs, and the like.

It is to be understood that individuals placed on dithiocarbamate disulfide or thiolate anion therapy for their cancer in any form must be warned against exposure to alcohol in any form, to avoid the precipitation of nausea and vomiting from buildup of acetaldehyde in the bloodstream. Subjects therefore must not only refrain from ingesting alcohol containing beverages, but should also not ingest over the counter formulations such as cough syrups containing alcohol or even use rubbing alcohol topically.

Experimental Procedures

Materials.

Human malignant cell lines were obtained from American Type Tissue Culture Collection (Rockville, Md.). RPMI medium 1640, Leibovitz's L-15 medium, N-2-hydroyethylpiperazine-N'-2-ethanesulfonic acid (HEPES), antibiotic-antimycotic (10,000 U penicillin, 10,000 μg streptomycin, and 25 μg amphotericin B/ml), fetal bovine serum (FBS) and trypsin-ethylenediaminetetraacetic acid (EDTA) solution were purchased from the GIBCO-BRL division of Life Technologies (Grand Island, N.Y.). Rabbit polyclonal antibodies against human Bcl-2, p53, p21$^{WAF1Cip1}$ cyclins A and B1, CREB1, ATF1, ATF2, c-Jun and Jun B were from Santa Cruz Biotechnology (Santa Cruz, Calif.). Rabbit polyclonal antibody against c-Fos and A431 cell lysate standard were from Calbiochem (San Diego, Calif.). Peroxidase-labeled donkey polyclonal anti-rabbit IgG was from Amersham Life Sciences (Buckinghamshire, England), and peroxidase-labeled anti-goat IgG was from Santa Cruz Biotechnology. Electrophoretic mobility shift assay (EMSA) supplies, including DNA probes, were purchased from ProMega (Madison, Wis.). Protease inhibitors were from Boehringer Mannheim (Indianapolis, Ind.). The diacetate of 2',7'-dichlorofluorescin (DCF-DA) was purchased from Molecular Probes (Eugene, Oreg.). Pyrrolidinedithiocarbamate (PDTC), diethyldithiocarbamate, tetraethylthiuram disulfide (di sulfiram), bathocuproinedisulfonic acid (BCPS), metal salts, nonenzymatic Cell Dissociation Solution®, Nω-nitro-L-arginine, indomethacin, bovine serum albumin (BSA) and all other materials were purchased from Sigma Chemical Co. (St. Louis, Mo.), unless specified.

Culture of Malignant Cell Lines.

Human malignant cell lines were obtained from American Type Tissue Culture Collection (Rockville, Md.). Melanoma cells lines CRL 1585 and 1619 were cultured in RPMI1640 (GIBCO-BRL, Life Technologies, Grand Island, N.Y.) with 10% FBS and passed with nonenzymatic Cell Dissociation Solution® (Sigma). The prostate adenocarcinoma cell line CRL 1435 (PC-3) was also cultured in RPMI 1640 with 10% FBS but passed with 0.05% trypsin and 0.53 mM EDTA. The squamous lung carcinoma NCI-H520 and the adenosquamous lung carcinoma NCI-H596 cell lines were grown in RPMI1640 supplemented with 10% FBS, 10 mM HEPES and 1.0 mM sodium pyruvate and passed with trypsin/EDTA. The small cell lung carcinoma NCI-H82 was cultured as a suspension in RPMI 1640 with 10% FBS. All of the above were grown in a 37° C. humidified environment containing 5% $CO_2$/air. The breast carcinoma cell line MDA-MB-453 was grown in a 37° C. humidified environment with free gas exchange with atmospheric air using Leibovitz's L-15 medium with 2 mM L-glutamine and 10% FBS and was passed with trypsin/EDTA.

Cell Culture Treatments.

Because the disulfide form of dithiocarbamates does not have a free thiol to act as an antioxidant, most of the experiments were performed with the tetraethylthiuram disulfide disulfiram. To study the effect of disulfiram on activation of select genes important for cellular proliferation, malignant melanoma cells were grown to confluence on 100×15 mm plastic Petri dishes and treated with 5 μM disulfiram or 5 μM disulfiram plus 1.6 μM $CuSO_4$. This dose was chosen to approximate the steady state plasma and tissue concentrations of drug in human subjects on chronic therapy with this agent. Disulfiram was solubilized in dimethylsulfoxide (DMSO) so that the final concentration of DMSO was less than 0.3–0.5%. Equal volumes of DMSO were added to control experiments. Nuclear protein was harvested and electrophoretic mobility gel shift assays were performed using DNA consensus binding sequence for the cyclic-AMP responsive element (CRE) as outlined below. To determine whether disulfiram and metals might directly influence transcription factor binding, in some experiments, 5 μM disulfiram and/or $CuSO_4$ 1.6 μM $CuSO_4$ (final concentrations) were added to the binding reaction of nuclear protein obtained from control cells stimulated with 10% FBS alone in the absence of drugs or metals. In vitro addition of disulfiram and $CuSO_4$ to the binding reaction was performed using either 2.5 mM dithiothreitol (DTT) or 3.0 mM GSH as a reducing agent in the binding buffer.

The effect of disulfiram (0.15 to 5.0 μM), diethyldithiocarbamate (DDC, 1.0 μM) or PDTC (0.625 to 5.0 μM) on proliferation of malignant cell lines was studied in cultures stimulated with 10% FBS. Cell numbers were quantitated 24–72 hours later. In some experiments disulfiram or PDTC were added immediately after cells were plated. In other experiments, cells were plated and allowed to grow for 24–72 hours before fresh media with disulfiram or PDTC was added, and cell numbers were assayed 24–72 hours later. Synergy was studied between disulfiram and N,N'-bis (2-chloroethyl-N-nitrosourea (carmustine or BCNU, 1.0 to 1,000 μM) or cisplatin (0.1 to 100 μg/ml) added to medium. The effect of metals on disulfiram was studied with 0.2 to 10 μM copper (provided as $CuSO_4$), zinc (as $ZnCl_2$), silver (as silver lactate) or gold (as $HAuCl_{4-3}H_2O$) ions added to growth medium. No pH changes occurred with addition of metal salts to culture medium. To provide a biologically relevant source of copper, in some experiments medium was supplemented with human ceruloplasmin at doses replicating low and high normal adult serum concentrations (250 and 500 μg/ml).

Potential redox effects of disulfiram were studied in three sets of experiments. The importance of cellular glutathione (GSH) in mediating or modulating thiocarbamate toxicity was studied by measuring levels of intracellular GSH after treatment with disulfiram. Disulfiram (5 μM), with or without 1.6 μM $CuSO_4$, was added to cells grown to confluence on 100×15 mm plastic dishes, and cells were harvested 24 hour later for measurement of GSH as outlined below. Also, to assess whether a nonspecific antioxidant effect of disulfiram or PDTC might account for cellular growth inhibition, we studied the effect of the potent lipophilic antioxidant probucol (1.0 to 1,000 μM) on proliferation of malignant cell lines. Finally, the generation of intracellular oxidants in response to disulfiram (0.625 to 5 μM), copper (0.2 to 1.6 μM $CuSO_4$) or 1.25 μM disulfiram plus various concentration of copper was measured directly.

To explore the role of cyclooxygenase inhibition on tumor cell growth, cells were cultured with or without disulfiram in the presence or absence of the cyclooxygenase-1 (COX1) and cyclooxygenase-2 (COX2) inhibitors indomethacin (5 μg/ml) or sodium salicylate (1 mM). To probe whether disulfiram might be inducing growth retardation by interruption or stimulation of NO production, proliferation was studied with and without disulfiram in the presence and absence of the nitric oxide synthese inhibitor Nω-nitro-L-arginine added to growth medium (100 μM).

Finally, a number of dithiocarbamate effects on cells have been attributed to increasing the intracellular levels of copper ions. To further probe the role of copper in mediating cytotoxicity from disulfiram, cells were cultured with or without addition of the impermeate $CuCu^{2+}$ chelator bathocuproinedisulfonic acid (BCPS, 100 μM) added to medium to sequester $CuCu^{2+}$ in the extracellular compartment. Cells were also treated 12 hours with various concentration of disulfiram (0.625 to 5.0 μM) and intracellular copper levels were measured as outlined below.

Electrophoretic Mobility Shift Assays (EMSAs).

Nuclear protein was isolated and DNA binding reactions were performed as previously described in detail (See, e.g., R. Dashtaki, et al., "Dehydroepiandrosterone and analogs inhiibit DNA binding of AP-1 and airway smooth muscle proliferation," *J. Pharmacol. Exper. Ther.* 285:876–219 (1998); T. Kennedy, et al., "Copper-dependent inflammation and nuclear factor-κB activation by particulate air pollution," *Am. J. Respir. Cell Mol. Biol.* 19:366–378 (1998)). Monolayers were washed twice in cold DPBS and equilibrated 10 minutes on ice with 0.7 ml cold cytoplasmic extraction buffer, CEB (10 mM Tris, pH 7.9, 60 mM KCl, 1 mM EDTA, 1 mM DTT) with protease inhibitors, PI (1 mM Pefabloc, 50 μg/ml antipain, 1 μg/ml leupeptin, 1 μg/ml pepstatin, 40 μg/ml bestatin, 3 μg/ml E-64 and 100 μg/ml chymostatin). The detergent Nonidet P-40 (NP-40) was added to a final concentration of 0.1% and cells were dislodged with a cell scraper. Nuclei were pelleted by centrifugation and washed with CEB/PI. Nuclei were then incubated for 20 minutes on ice in nuclear extraction buffer, NEB (20 mM Tris, pH 8.0, 400 mM NaCl, 1.5 mM $MgCl_2$, 1.5 mM EDTA, 1 mM DTT and 25% glycerol) with PI, spun briefly to clear debris and stored at −80° C. until performance of electrophoretic mobility shift assays.

EMSAs were performed using consensus oligonucleotides (5'-AGAGATTGCCTGACGTCAGAGAGCTAG-3' and 3'-TCTCTAACGGACTGCAGTCTCTCGATC-5') for the cyclic-AMP responsive element CRE (ProMega, Madison, Wis.), end-labeled by phosphorylation with [$\gamma^{32}P$]-ATP and T4 polynucleotide kinase. DNA-protein binding reactions were performed with 2 μg of nuclear protein (as determined by the Pierce method) and 30–80,000 cpm of $^{32}P$-end-labelled double-stranded DNA probe in 10 mM Tris-HCl, pH 7.5, 50 mM NaCl, 0.5 mM EDTA, 0.5 mM DTT (except where indicated), 1 mM $MgCl_2$, 50 μg/ml poly dI-dC, and 4% glycerol. All components of the binding reaction with the exception of labeled probe were combined and incubated at room temperature for 10 minutes before addition of labeled probe and incubation for an additional 20 minutes.

Competition experiments were performed with 10× unlabeled wild-type oligonucleotide sequences for CRE or NF-κB (p50, 5'-AGTTGAGGGGACTTTCCCAGGC-3' and 3'-TCAACTCCCCTGAAAGGGTCCG-5'), added before labeled probe. Supershift experiments were performed by incubating the binding reaction with 1 μg of supershifting antibody prior to electrophoresis. Samples were electrophoresed on a 5% nondenaturing polyacrylamide gel in Tris-glycine-EDTA (TGE, 120 mM glycine and 1 mM EDTA in 25 mM Tris, pH 8.5) buffer. Gels were dried and analyzed by autoradiography at −80° C. using an image intensifier screen. Densitometry of bands was performed using Kodak Digital Science 1D image analysis software (Eastman Kodak, Rochester, N.Y.).

Measurement of Proliferation in Cell Cultures

Proliferation of cultured cells was quantitated using a previously reported colorimetric method based upon metabolic reduction of the soluble yellow tetrazolium dye 3-[4,5-dimnethylthiazol]-2yl-2,5-diphenyl tetrazolium bromide (MTT) to its insoluble purple formazan by the action of mitochondrial succinyl dehydrogenase (See, e.g., S. J. Hirst, et al., "Quantifying proliferation of cultured human and rabbit airway smooth muscle in response to serum and platelet derived growth factor," *Am. J. Respir. Cell Mol. Biol.* 7:574–581 (1992); R. Dashtaki, et al. R., supra; S. S. Brar, et al., "Requirement for reactive oxygen species in serum-induced and platelet-derived growth factor-induced growth of airway smooth muscle," *J. Biol. Chem.* 274:20017–20026(1999)). This assay empirically distinguishes between dead and living cells. For proliferation studies, cells were seeded into 24-well uncoated plastic plates (Costar) at 50,000 cells per well and cultured with respective media and mitogens. After 24–96 hours, medium was removed, cells were washed twice with 1 ml of sterile Dulbecco's modified phosphate buffered saline without $CaCu^{2+}$ or $MgCu^{2+}$ (DPBS), the medium was replaced with 1 ml/well fresh medium containing 100 μg/ml MTT, and plates were incubated an additional hour. MTT-containing medium was removed, 0.5 ml dimethylsulfoxide (DMSO) was added to each well, and the absorbance of the solubilized purple formazan dye was measured at 540 nm. A total of 4–6 wells were studied at each treatment condition. Preliminary studies were performed with 50–200 μg/ml MTT incubated for 15 minutes to 3 hours to determine the optimum concentration and incubation time at which the rate of conversion was linear and proportional to the number of cells present. The absorbance of the MTT formazan reduction product ($A_{540}$) correlated with cell numbers counted by hemocytometer with an $R^2=0.99$. In some experiments, the MTT assay and responses to FBS and inhibitors were also confirmed by performing cell counts on 10 random fields/well of Giemsa-modified Wright's stained monolayers viewed at 40 power using a 0.01-$cm^2$ ocular grid.

Measurement of Cytotoxicity and Apoptosis

To assess for cytotoxicity, cells were plated at a density of 50,000 per well on 24 well plates and grown for 24 hours. Disulfiram was then added. After an additional 36 hours, medium was removed and replaced with DPBS containing 0.1% trypan blue. Cell death was assessed by counting the average number of trypan blue positive cells per 10× field in 5 random fields for 4 separate wells.

To determine whether disulfiram induced apoptosis, cells grown to confluence on 35 mm Petri dishes or on glass slides were treated with disulfiram or DMSO as vehicle. Apoptosis was studied by terminal deoxynucleotidyl transferase (TdT) dependent 3'-OH fluorescein end-labeling of DNA fragments, using a Fluorescein-FragEL™ DNA fragmentation detection kit (Oncogene Research Products, Cambridge, Mass.). Apoptosis was also studied by visually assessing endonuclease dependent DNA fragmentation on ethidium bromide-stained agarose gels.

DNA Cell Cycle Measurements

To study the effect of disulfiram on the DNA cell cycle, cells were grown to confluence in 25 $cm^2$ plastic flasks and treated for with 10% FBS plus DMSO vehicle, FBS and DMSO vehicle plus 250 µg/ml ceruloplasmin as a source of copper, FBS plus 5 µM disulfiram or FBS plus 5 µM disulfiram and 250 µg/ml ceruloplasmin. After 24 hours cells were trypsinized, washed twice in cold DPBS with 1 mM EDTA and 1% BSA, fixed 30 minute in ice-cold 70% ethanol, and stained by incubation for 30 minutes at 37° C. in a 10 µg/ml solution of propidium iodide in DPBS and 1 mg/ml RNase A. DNA cell cycle measurements were made using a FACStar$^{PLUS}$ Flow Cytometer (Becton-Dickenson, San Jose, Calif.).

Immunoassay for Proteins

Cells were lysed and proteins were isolated and quantitated by immunoassay as previously detailed using 2 µg/ml of primary rabbit polyclonal antibodies against human bcl-2, p53, p21$^{WAF1/Cip1}$, cyclin A and cyclin B1, and peroxidase-labeled donkey polyclonal, anti-rabbit IgG. Cells were placed on ice, washed twice with cold DPBS, scraped into 0.5 ml boiling buffer (10% [vol/vol] glycerol and 2% [wt/vol] sodium dodecyl sulfate [SDS] in 83 mM Tris, pH 6.8) and sheared by four passages through a pipette. Aliquots were removed for protein determination, using the BCA protein assay (Pierce). After 10% β-mercaptoethanol and 0.05% bromophenol blue were added, lysates were boiled for 5 min and stored at −80° C. until immunoblotting was performed. Proteins in defrosted samples were separated by SDS-polyacrylamide gel electrophoresis on 12% polyacrylainide gels (15 µg protein/lane) and electrotransferred to 0.45 µm Hybond ECL nitrocellulose membranes (Amersham Life Sciences) using the wet transblot method in transfer buffer (0.025 M Tris, 0.192 M glycine, 2.6 mM SDS, and 20%[vol/vol] methanol; pH 8.8) at 100 volts for 1 hour. Blots were blocked overnight at 4° C. with blocking buffer (PBS with 0.1% Tween 20) containing 5% fat-free milk powder (Carnation, Glendale, Calif.). After rinsing 5 times for 5 minutes each in PBS containing 0.1% Tween 20, blots were incubated for 1 hour at room temperature with 2.0 µg/ml of primary antibody. After rinsing again as above, blots were incubated for 1 hr at room temperature with horseradish peroxidase(HRP)-conjugated secondary antibody diluted 1:5,000 in blocking buffer. Immunoblots were rinsed again as above and detected via an enhanced chemiluminescence method (ECL Western blotting detection system, Amersham Life Science, Buckinghamshire, England). Autoradiographic film (X-OMAT AR, Eastman Kodak, Rochester, N.Y.) was exposed to immunoblots for 10, 30, or 60 seconds to obtain satisfactory images.

Measurement of Intracellular Copper

Cells were cultured in 12-well plastic tissue culture plates at an initial plating density of 50,000 cells/well, grown to confluence and treated with disulfiram or vehicle DMSO as outlined above. Media was removed and cells were washed twice with DPBS. Cells were then scraped into 1.0 ml of 3N HCl/10.0% trichloroacetic acid and hydrolyzed at 70° C. for 16 hours. The hydrolysate was centrifuged at 600 gm for 10 minutes to remove debris and copper was measured in the supernatant using inductively coupled lasma emission spectroscopy (Model P30, Perkin Elmer, Norwalk, Conn.) at wavelengths of 325.754 and 224.700 nm. To minimize metal contamination, plasticware rather than glassware was used in these experiments, and double-distilled, deionized water was used for all aqueous media. Results are reported as ng copper/ml of hydrolysate.

Measurement of Intracellular Generation of Reactive Oxygen Species

Generation of reactive oxygen species in response to disulfiram with or without $CuSO_4$ was studied using 2',7'-dichlorofluorescin diacetate (DCF-DA, Molecular Probes, Eugene, Org.) and a modification of methods previously reported (See, J. A. Royall, et al., "Evaluation of 2',7'-dichlorofluorescin and dihydrorhodamine 123 as fluorescent probes for intracellular $H_2O_2$ in cultured endothelial cells," Archiv. Biochem. Biophys. 302:348–355 (1993)). This method is based upon oxidation of dichlorofluorescin to 2',7'-dichlorofluorescein by $H_2O_2$ in the presence of cellular peroxidases. Cells were plated in 24 well plastic plates at 50,000 cells per well and grown to confluence. Media was aspirated from wells and replaced with 100 µl medium containing 10 µM DCF-DA, and plates were incubated at 37° C. for 30 minutes. The DCF-DA containing media was aspirated, cells were washed twice with media alone and 100 µl fresh media was added to wells. With the plate on the fluorescence micro-plate reader (HTS 7000) cells were stimulated with 25 µl of media containing 5 × concentrations of disulfiram and/or $CuSO_4$ to provide final concentrations of 0–5.0 µM disulfiram and/or 0–1.6 µM $CuSO_4$, respectively. The relative concentration of dichlorofluroescein was measured immediately by monitoring fluorescence at 37° C. using an excitation wavelength of 485 nm and emission wavelength of 535 nm.

Measurement of Intracellular Glutathione

Disulfiram (5 µM), with or without 1.6 µM $CuSO_4$, was added to cells grown to confluence on 100×15 mm plastic dishes, and cells were harvested 24 hours later for measurement of GSH using the 5,5'-dithiobis(2-nitrobenzoic acid)-glutathione reductase recycling assay (See, M. E. Anderson, "Determination of glutathione and glutathione disulfide in biological samples," Methods Enzymol. 113:548–555 (1985)).

Synthesis of Disulfiram-Metal Chelates

Chelates of disulfiram and a number of metals were synthesized by vigorous mixing of 150 mg of disulfiram in chloroform (7.5 mg/ml) with 30 ml of a 5× molar excess of $CuSO_4$, $ZnCl_2$, $C_3H_5AgO_3$ (silver lactate) or $HAuCl_4.3H_2O$ in double glass distilled deionized water. The mixture was centrifuged at 1,000 µm for 10 minutes and the upper aqueous phase was discarded. As the lower chloroform phase was evaporated, the resulting disulfiram-metal chelates precipitated.

In another synthesis, 150 mg of sodium diethyldithiocarbamate was dissolved in 10 ml of deionized water. To this was added 250 mg of $HAuCl_4 \cdot 3H_2O$. The resulting precipitate was collected by centrifugation and redisolved in chloroform. As the chloroform phase was evaporated the resulting dithiocarbamate-gold chelates were precipitated as crystals.

These were analyzed to determine their molecular weight, melting point, solubility, elemental composition and crystallographic structure.

Statistical Analysis

Data are expressed as mean values±standard error. The minimum number of replicates for all measurements was four, unless indicated. Differences between multiple groups were compared using one-way analysis of variance. The post-hoc test used was the Newman-Keuls multiple comparison test. Two-tailed tests of significance were employed. Significance was assumed at $p<0.05$.

EXAMPLE 1

This example shows dithiocarbamate disulfides inhibit DNA binding to the cyclic AMP response element.

Figure 1B:
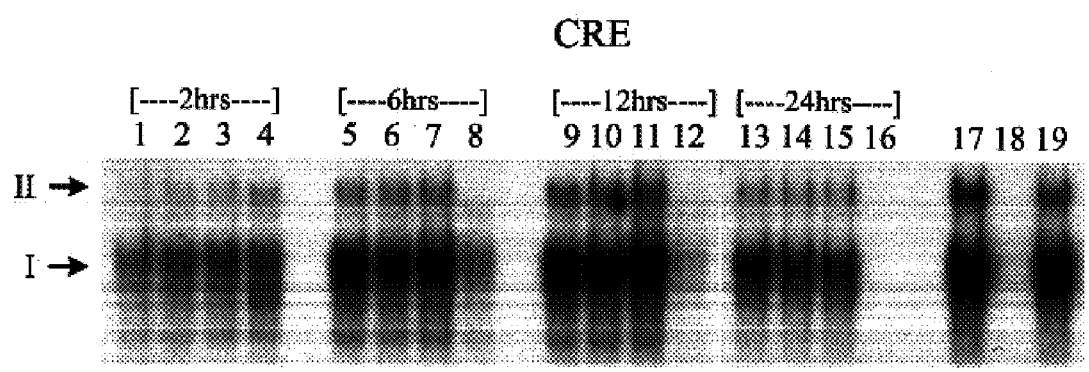
FIG. 1B shows that the thiocarbamate disulfide disulfiram and copper inhibit transcription factor binding to CRE.
Figure 1C:
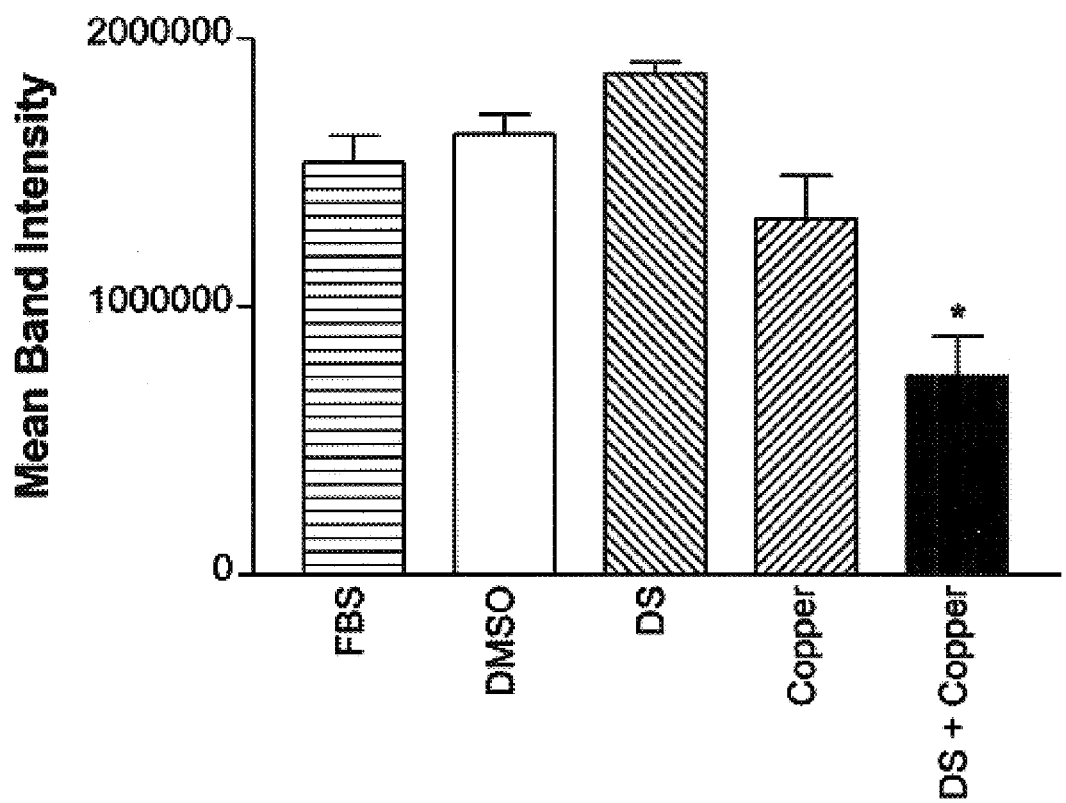
FIG. 1C shows that EMSAs performed using nuclear protein from replicate experiments (n=4) in which near confluent cells were treated for 8 hr with FBS alone, DMSO vehicle (5 µl/well), disulfiram (5 µM), CuSO$_4$ (1.6 µM), or the combination of disulfiram plus copper.

M1619 melanoma cells were grown to 60% confluence on 100×15 mm plastic Petri dishes, nuclear protein was harvested and electrophoretic mobility gel shift assays (EMSAs) were performed using. The results are shown in FIGS. 1A–1C. Treatment of cells for 6, 12 or 24 hour with the combination of 5 $\mu$M disulfiram and 1.6 $\mu$M cupric sulfate substantially interrupts transcription factor binding to CRE. EMSAs for 2, 6, 12 or 24 hours of treatment: FBS alone, lanes 1, 5, 9, and 13; FBS+DMSO vehicle, lanes 2, 6, 10, 14; FBS+disulfiram, lanes 3, 7, 11, 15; FBS+disulfiram+$CuSO_4$, lanes 4, 8, 12, 16.

CRE complexes (I and II) are labeled. Nuclear protein from proliferating M1619 malignant melanoma cells showed two strong constitutive bands (I and II) of DNA binding activity in electrophoretic mobility shift assays with the cyclic AMP response element (CRE) consensus sequence (FIG. 1A, lane 1). Both bands were eliminated by addition of 10× unlabeled CRE consensus oligonucleotide to the binding reaction (lane 8). Supershift experiments demonstrated that the top band II contains the CRE binding protein activating transcription factor-2 (ATF-2, lane 5), while the lower complex I contains CREB-1 (lane 2), with ATF-1 (lane 4) as a minor component. Competition experiments shown in lanes 6–8 demonstrate specificity of the DNA binding reaction: lane 6, FBS :(fetal bovine serum) alone; lane 7, FBS with 10× unlabeled CRE probe added to binding reaction; lane 8, FBS with 10× unlabeled NF-κB probe added to binding reaction.

As shown in FIG. 1B, disulfiram alone slightly reduced DNA-binding to CRE, but when combined with treatment of cells with the transition metal copper, disulfiram eliminated transcription factor binding to CRE after 6 hours of treatment.

The upper ATF-2 containing complex proved more sensitive to inhibition. This is demonstrated in FIG. 1C, which shows densitometry results performed on the ATF-2 containing upper complex II experiments is displayed as mean sum intensity of bands. The EMSAs in replicate experiments (n=4) in which near confluent cells were treated for 8 hours with DMSO vehicle, disulfiram, copper or the combination of disulfiram plus copper. The combination of disulfiram plus copper reduced DNA binding of the upper complex II by half suggests that ATF-2 is extremely sensitive to inhibition by interactions between thiuramdisulfides and some metals. At the concentrations employed above, disulfiram plus copper also inhibited DNA binding of NF-κB after treatment for 12 hours and DNA binding of AP-1 after 24 hours (data not shown), but effects were not as dramatic those on binding to CRE.

Figure 2:
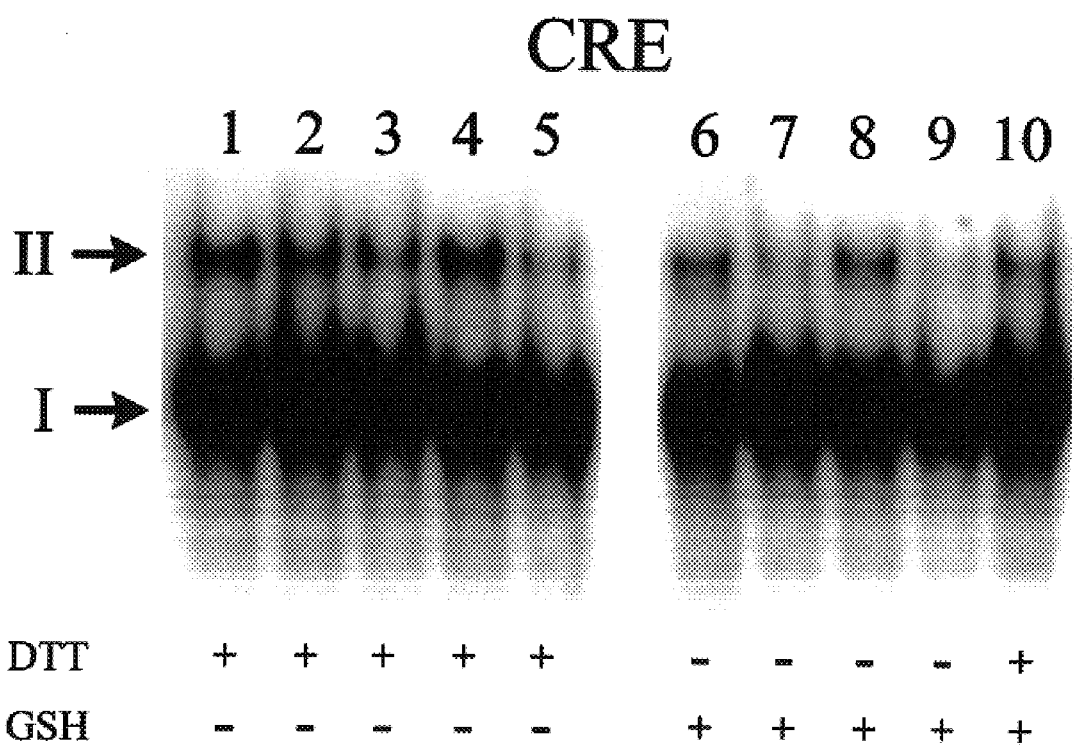
FIG. 2 shows the effect of adding disulfiram or disulfiram plus copper directly to binding reaction on transcription factor to DNA binding.

To determine if inhibition of transcription factor binding to CRE could be attributed to direct transcription factor modification by disulfiram and copper, we studied the effect of adding each agent directly to the binding reaction performed with nuclear protein from untreated M1619 cells. The results are shown in FIG. 2. Therein electrophoretic mobility shift assays (EMSAs) were performed showing that addition of disulfiram plus copper to the binding reaction reduces DNA binding to CRE. Lane 1, nuclear protein from fetal bovine serum-stimulated M1619 cells (FBS); lane 2, FBS+DMSO vehicle; lane 3, FBS+disulfiram (5 $\mu$M); lane 4, FBS+1.6 $\mu$M $CuSO_4$; lane 5, FBS+disulfiram+$CuSO_4$; lane 6, FBS alone; lane 7, FBS+disulfiram; lane 8, FBS+$CuSO_{4;\ lane}$ 9, FBS+disulfiram+$CuSO_4$; lane 10, FBS+disulfiram+CuSO4. In lanes 1–5, DTT (2'.5 mM) was added to the binding reaction as a reducing agent, whereas in lane 6–9, GSH (3.0 mM) was used. Disulfiram alone (lane 3) or disulfiram and copper (lane 5) reduced transcription factor binding to CRE, but the effect of these agents was more pronounced when the binding reaction was performed with GSH (lanes 7 and 9) instead of DTT (lane 3 and 5) as the reducing agent. Inhibition of binding to CRE by disulfiram and copper in the presence GSH was reversed by simultaneous addition of the more potent reducing agent DTT (lane 10).

The addition of disulfiram alone to the binding reaction reduced DNA binding to CRE in the Upper ATF2 containing complex II (FIG. 2, lane 3). This effect was magnified when disulfiram was combined with copper ions (lane 5). These results are consistent width modest disruption of ATF2 binding to CRE from formation of mixed disulfides between disulfiram and cysteines in the DNA binding region, and suggest that copper catalyzes mixed disulfide generation. However, reduction in CRE binding was much more pronounced when the binding reaction was performed with GSH instead of DTT as the reducing agent (FIG. 2, lane 7 for disulfiram, lane 9 for disulfiram plus copper). Inhibition of ATF2 containing complex II binding to CRE by disulfiram and copper in the presence of GSH was reversed by simultaneous addition of the potent uncharged reducing agent DTT (FIG. 2, lane 10).

These results indicate that GSH, a cellular monothiol found in mM concentrations within the nuclear compartment might react with the dithiocarbamate adduct leading to a bulky, negatively charged GSH-containing mixed disulfide that could more effectively disrupt DNA binding of ATF2.

EXAMPLE 2

This example shows that dithiocarbamate disulfides and copper inhibit cyclin A expression. It is known that heterodimers of the transcription factors CREB-1 and c-Fos or ATF2 and Jun family members positively regulate cyclin-A expression through binding to a CRE element in the cyclin A promoter.

Figure 3A:
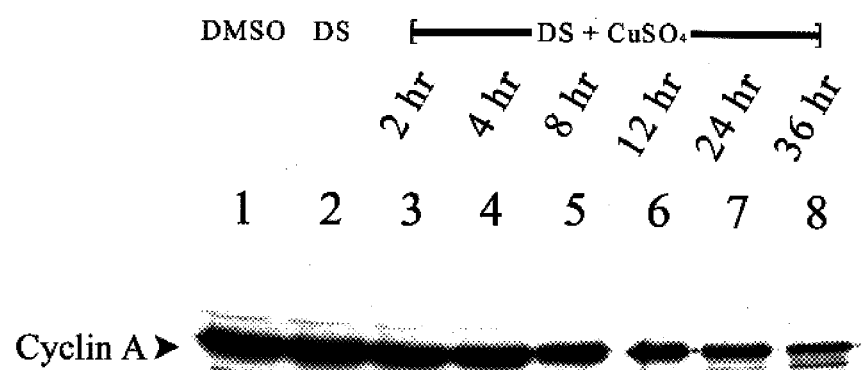
FIG. 3A shows disulfiram and copper reduce expression of the cell-cycle protein cyclin A.

Since disulfiram and copper disrupt transcription factor DNA binding to CRE, their effect on expression of cyclin A was studied. FIG. 3A shows disulfiram and copper reduce expression ofthe cell-cycle protein cyclin A. M1619 melanoma cells were plated at equal densities in 60×15 mm plastic dishes, grown to 80% confluence and treated with DMSO vehicle (5 $\mu$l/ml), disulfiram (DS, 5 $\mu$M), or the combination of disulfiram and $CuSO_4$ (1.6 μM). After the indicated times, cells were lysed and protein extracts were subjected to SDS-polyacrylamide gel electrophoresis (PAGE) followed by Western blotting using a rabbit polyclonal antibody (Santa Cruz). Typical experiments are shown for 2, 4, 8, 12, 24 and 36 hours of treatment with disulfiram plus $CuSO_4$.

Figure 3B:
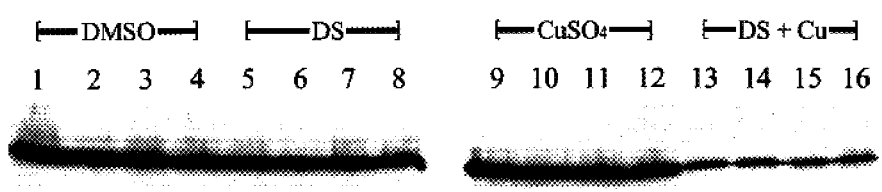
FIG. 3B replicates experiments (n=4 each) in which cells were treated with DMSO vehicle, (5 µl/ml, lanes 1–4), disulfiram (5 µM, lanes 5–8), (5 µl/ml), CuSO$_4$ (1.6 µM, lanes 9–12) or the combination of disulfiram and CuSO$_4$ (lanes 13–16). After 24 hours cells were lysed, immunoblots were performed to assay for cyclin A.
Figure 3C:
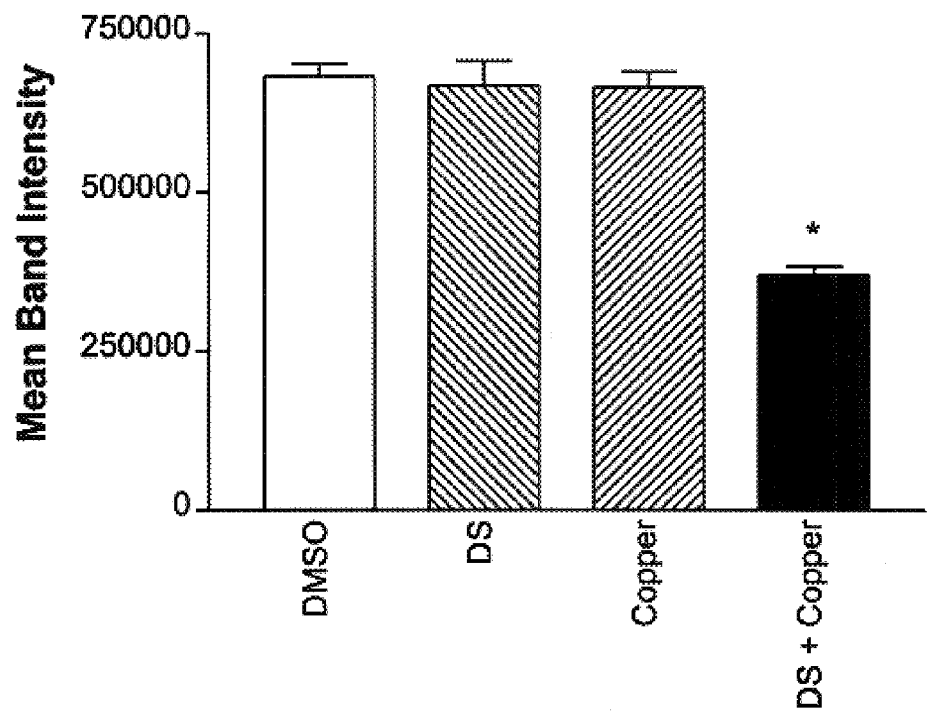
FIG. 3C illustrates quantitation of experiments in FIG. 3B by densitometry.

FIG. 3B replicates experiments (n=4 each) in which cells were treated with DMSO vehicle, (5 μl/ml, lanes 1–4), disulfiram (5 μM, lanes 5–8), (5 μl/ml), $CuSO_4$ (1.6 μM, lanes 9–12) or the combination of disulfiram and $CuSO_4$ (lanes 13–16). After 24 hours cells were lysed, immunoblots were performed to assay for cyclin A. In FIG. 3C shows quantitation of experiments in FIG. 3B by densitometry. Mean sum intensity of bands is displayed. *p<0.001 compared to all other treatments.

While disulfiram or copper alone had little effect (FIGS. 3B and C), treatment with the combination of disulfiram plus copper progressively decreased cyclin A expression over time (FIG. 3A) and reduced expression of cyclin A by over two-thirds at 24 hours (FIGS. 3B and 3C). In contrast, levels of B1 remained unchanged, and, in the cell lines we studied, disulfiram had no consistent effect on expression of the cell cycle inhibitor $p21^{WAF1/CIP1}$ or the pro- and anti-apoptotic proteins p53 or bcl-2 (data not shown).

EXAMPLE 3

Figure 4A:
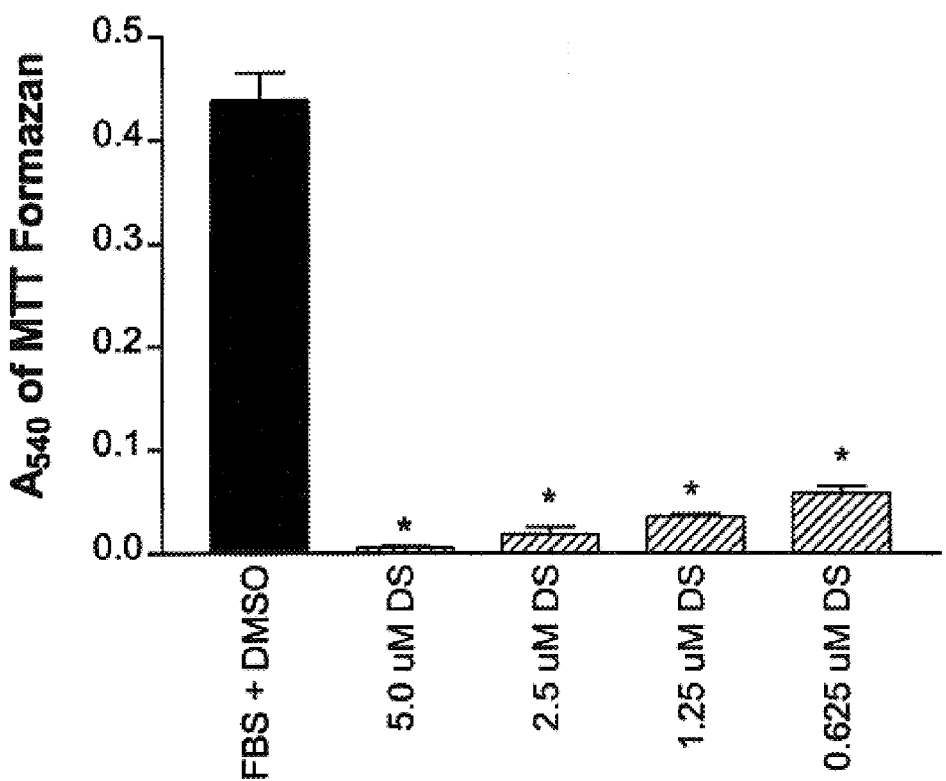
FIG. 4A shows that disulfiram inhibits proliferation of M1619 human melanoma, cell lines.

This example illustrates that disulfiram is antiproliferative against melanoma and other tumor cell lines. Disruption of cyclin A expression should impair cell cycle progression and cellular proliferation. Therefore, the effect of disulfiram on M1619 melanoma growth, using concentrations readily achieved in humans on usual clinical doses was studied. Disulfiram was a potent inhibitor of growth in vitro for M1619 melanoma (FIG. 4A). FIG. 4A shows that disulfiram inhibits proliferation of M1619 human melanoma cell lines. Cells stimulated with 10% fetal bovine serum (FBS) were plated at a density of 50,000 cells per well, and DMSO vehicle (5 μl per ml) or disulfiram (DS) was added to wells at the indicated concentrations. After 24 hours, proliferation was quantitated by assessing the cell number-dependent reduction of the soluble yellow tetrazolium dye 3-[4,5-dimethylthiazol]-2yl-2,5-diphenyl tetrazolium bromide (MTT) to its insoluble formazan, measured as the absorbance at 540 nm ($A_{540}$) (6,7). *p<0.01 compared to FBS+DMSO vehicle control.

Disulfiram also inhibited growth of a variety of other malignant cell lines, including M1585 melanoma, prostatic adenocarcinoma, non-small cell and small cell lung cancer, and adenocarcinoma of the breast (Table 1). This was true whether disulfiram was added to culture Each value represents mean±SE percent inhibition of growth comrpared to DMSO vehicle treated control cultures. Cells stimulated with 10% fetal bovine serum (FBS) were plated at a density of 50,000 cells per well. In some studies (treatment initially) DMSO vehicle (5 μl per ml) or disulfiram (DS) was added to wells at the indicated concentrations. After 48 hours, proliferation was quantitated as described in FIG. 4.

In other studies (treatment after 24 hours) cells were grown for 24 hours (M1619, M1585 and H596 lung) or 48 hours (breast). DMSO vehicle (5 μl per ml) or disulfiram (DS) was added to wells at the indicated concentrations. After an additional 24 hours (lung) or 48 hours (breast), proliferation was quantitated as described in FIG. 4. Percent inhibition of growth was calculated as $100×(1.0−A_{540}$ of MTT formazan in disulfiram treated cells/mean $A_{540}$ of MTT formazan in DMSO vehicle treated cells). In some cell lines, a modest (<10%) but statistically significant inhibitory effect was observed with DMSO vehicle alone. Each value represents a mean of at least 4 experiments. $^Ap<0.01$ compared to FBS+DMSO vehicle control.

TABLE 1

DISULFIRAM IS ANTIPROLIFERATIVE FOR MALIGNANT CELLS

| Cell Line | Mean Percent Inhibition of Growth Concentration of Disulfiram (μM) | | | |
|---|---|---|---|---|
| | 0.625 | 1.25 | 2.5 | 5.0 |
| Treatment initially | | | | |
| Melanoma M1585 | 100 ± 0$^A$ | 100 ± 0$^A$ | 100 ± 0$^A$ | 100 ± 0$^A$ |
| Prostate carcinoma CRL 1435 (PC-3) | 6 ± 6 | 29 ± 5$^A$ | 48 ± 2$^A$ | 86 ± 2$^A$ |
| Squamous lung carcinoma NCI-H520 | 76 ± 3$^A$ | 82 ± 4$^A$ | 77 ± 4$^A$ | 78 ± 3$^A$ |
| Adenosquamous lung carcinoma NCI-H596 | 47 ± 4$^A$ | 57 ± 4$^A$ | 50 ± 3$^A$ | 50 ± 4$^A$ |
| Small cell lung carcinoma NCI-H82 | 68 ± 3$^A$ | 76 ± 6$^A$ | 76 ± 5$^A$ | 72 ± 3$^A$ |
| Breast carcinoma MDA-MB-453 | 69 ± 4$^A$ | 94 ± 2$^A$ | 100 ± 0$^A$ | 100 ± 0$^A$ |
| Treatment after 24 hours | | | | |
| Melanoma M1619 | 59 ± 4$^A$ | 35 ± 4$^A$ | 39 ± 3$^A$ | 37 ± 4$^A$ |
| Melanoma M1585 | 74 ± 4$^A$ | 49 ± 7$^A$ | 41 ± 2$^A$ | 37 ± 6$^A$ |
| Lung carcinoma NCI-H596 | 30 ± 3$^A$ | 30 ± 3$^A$ | 29 ± 1$^A$ | 34 ± 3$^A$ |
| Breast carcinoma MDA-MB-453 | 26 ± 5$^A$ | 26 ± 2$^A$ | 39 ± 2$^A$ | 46 ± 4$^A$ |

Figure 4B:
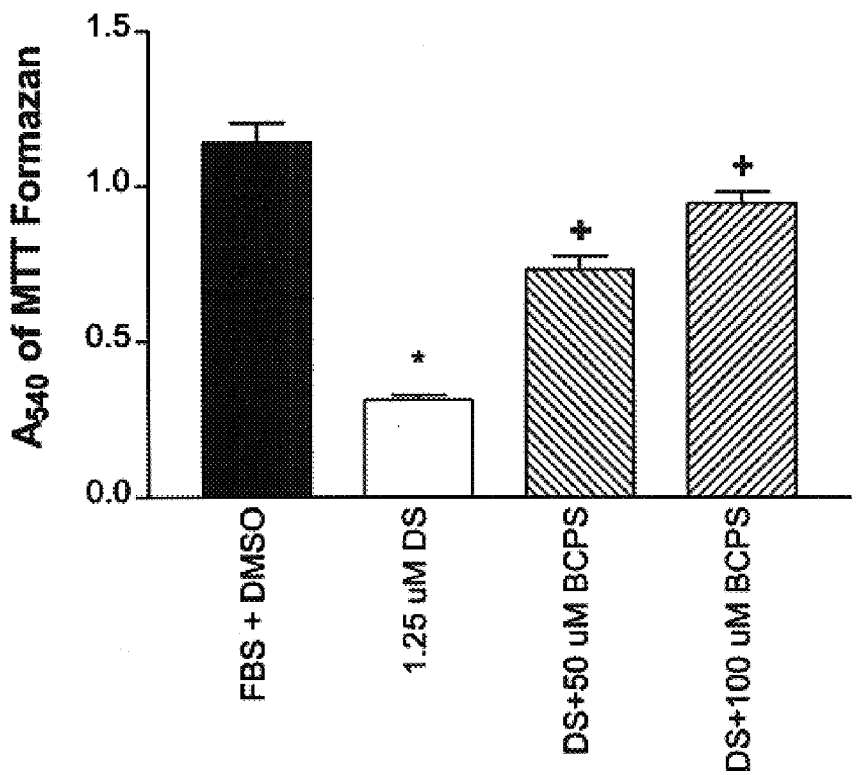
FIG. 4B illustrates that cell-impermeate $Cu^{2+}$ chelator bathocuproine-disulfonic acid prevents growth inhibition from disulfiram.

In FIG. 4B it is shown that the cell-impermeate $Cu^{2+}$ chelator bathocuproine-disulfonic acid prevents growth inhibition from disulfiram. M1619 melanoma cells stimulated and plated as described in A, and 1.25 μM disulfiram (DS) or DMSO vehicle (5 μl per ml) was added to wells in the absence or presence of 50 or 100 μM bathocuproine-disulfonic acid (BCPS). After 48 hr proliferation was quantitated as described. *p<0.001 compared to FBS+DMSO; +p<0.001 compared to FBS+DS.

Figure 4C:
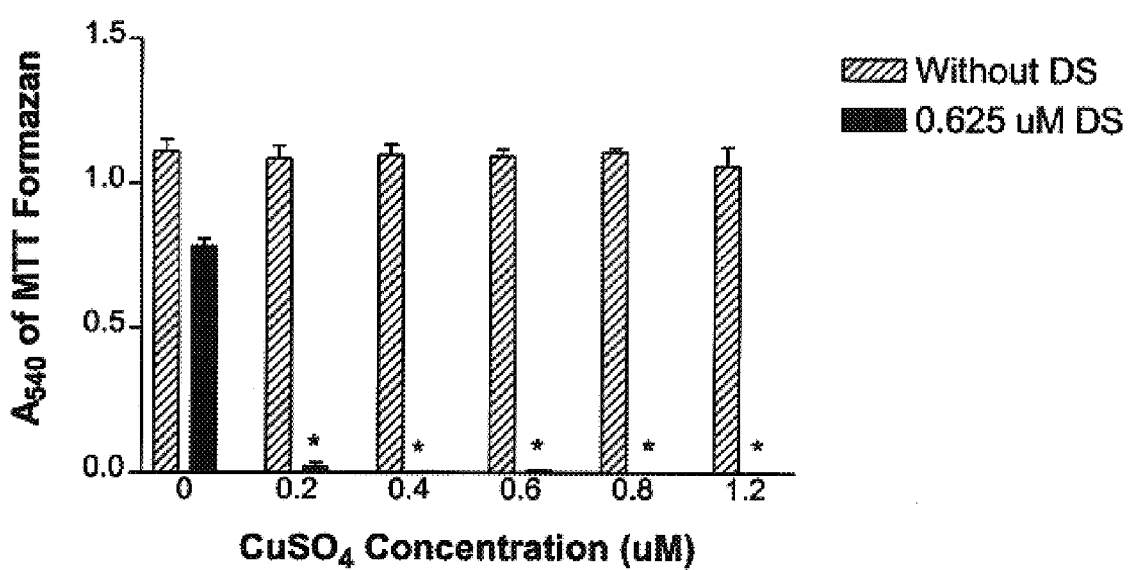
FIG. 4C sows supplementation of growth medium with copper enhances the antiproliferative activity of disulfiram.
Figure 4D:
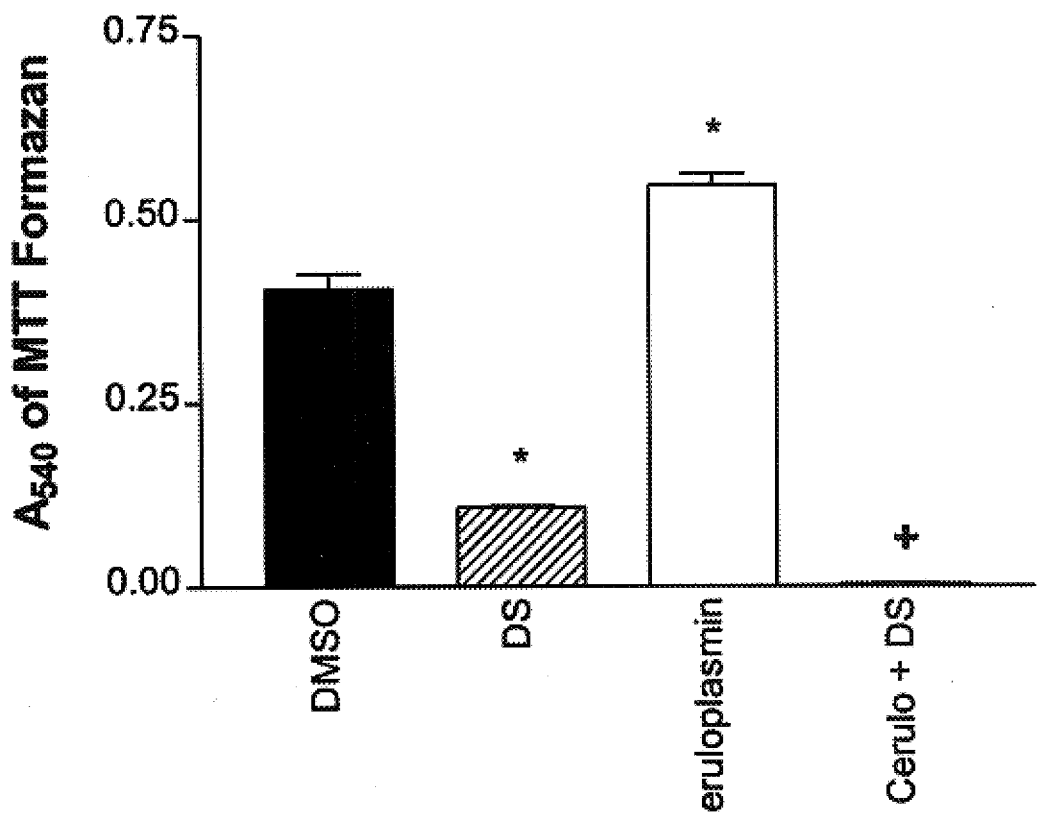
FIG. 4D shows that ceruloplasmin can serve as a source of copper for enhancing the antiproliferative activity of disulfiram.

FIG. 4C shows that supplementation of growth medium with copper enhances the antiproliferative activity of disulfiram. M1619 melanoma cells plated and stimulated as described in FIG. 4A were grown for 24 hours and supplemented with $CuSO_4$ or $CuSO_4$ plus, 0.625 μM disulfiram. After an additional 24 hours proliferation was quantitated. The addition of even 0.2 μM $CuSO_4$ to medium converts 0.625 μM disulfiram from a 50% inhibitory ($IC_{50}$) concentration (A) into a 100% inhibitory ($IC_{100}$) concentration of drug. *p<0.001 compared to no $CuSO_4$;

The results shown in FIG. 4D illustrate that ceruloplasmin can serve as a source of copper for enhancing the antiproliferative activity of disulfiram. M1619 melanoma cells were plated, stimulated and grown for 24 hours in the presence or absence of 0.625 μM disulfiram or 5 μl/ml DMSO vehicle in the presence or absence of human ceruloplasmin (Cerulo) at a concentration representing the upper level in normal human serum (500 μg/ml). After 24 hours proliferation was quantitated. *p<0.001 compared to FBS+DMSO; +p<0.001 compared to FBS+DS.

Disulfiram induced both necrosis and apoptosis. Treatment of monolayers with even low doses of disulfiram markedly increased trypan blue dye uptake (6±2, 8±3.6 and 94±18 trypan blue positive cells per well, respectively, for untreated, DMSO vehicle treated or H520 lung adenosquamous carcinoma cells treated with 0.625 $\mu$M disulfiram; 12±0.9, 16.5±2.1 and 93±12 trypan blue positive cells per well, respectively, for untreated, DMSO-treated or H82 small cell lung cancer cells treated with 0.625 $\mu$M disulfiram; p<0.001 compared to untreated or DMSO vehicle treated controls). Disulfiram also enhanced 3'-OH fluorescein end-labeling of DNA fragments (FIGS. 5A, and 5B) and DNA laddering on ethidium bromide-stained agarose gels (data not shown). Consistent with its recently reported effects on P-glycoprotein mediated drug resistance (See, T. W. Loo, et al., "Blockage of drug resistance in vitro by disulfiram, a drug used to treat alcoholism," *J. Natl. Cancer Inst.* 92:898–902 (2000)), disulfiram augmented the antiproliferative effect of other antineoplastic agents on melanoma cells, a tumor notoriously resistant to chemotherapeutic drugs.

Figure 5A:
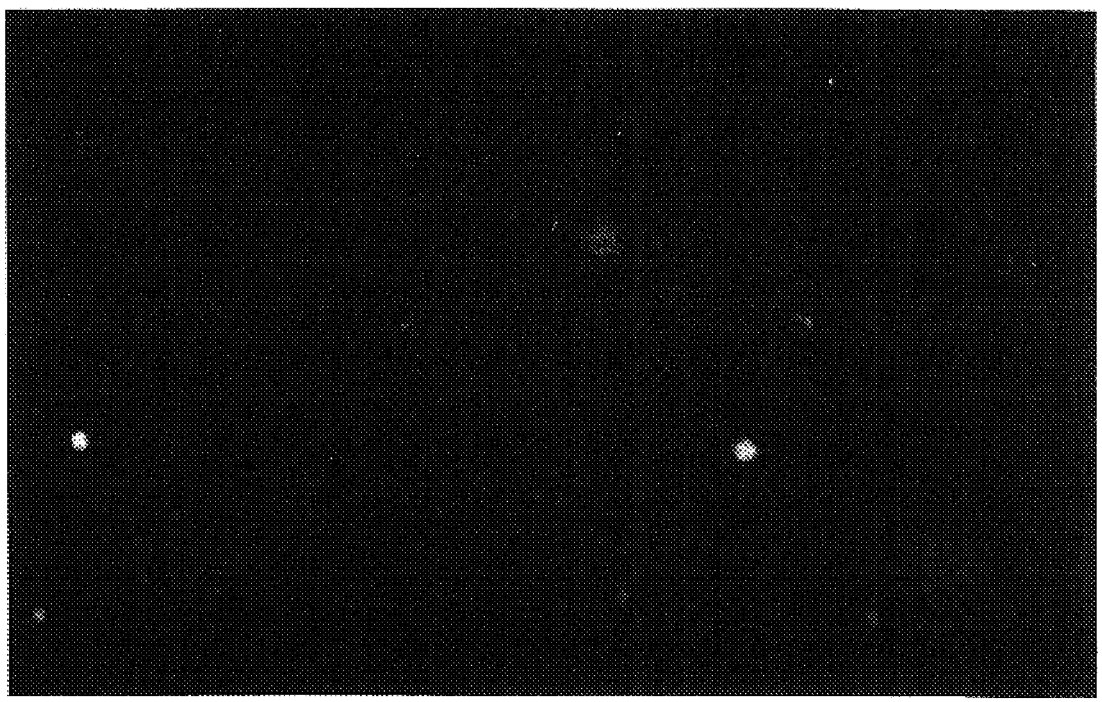
FIG. 5A shows M1619 melanoma cells treated with DMSO vehicle.
Figure 5B:
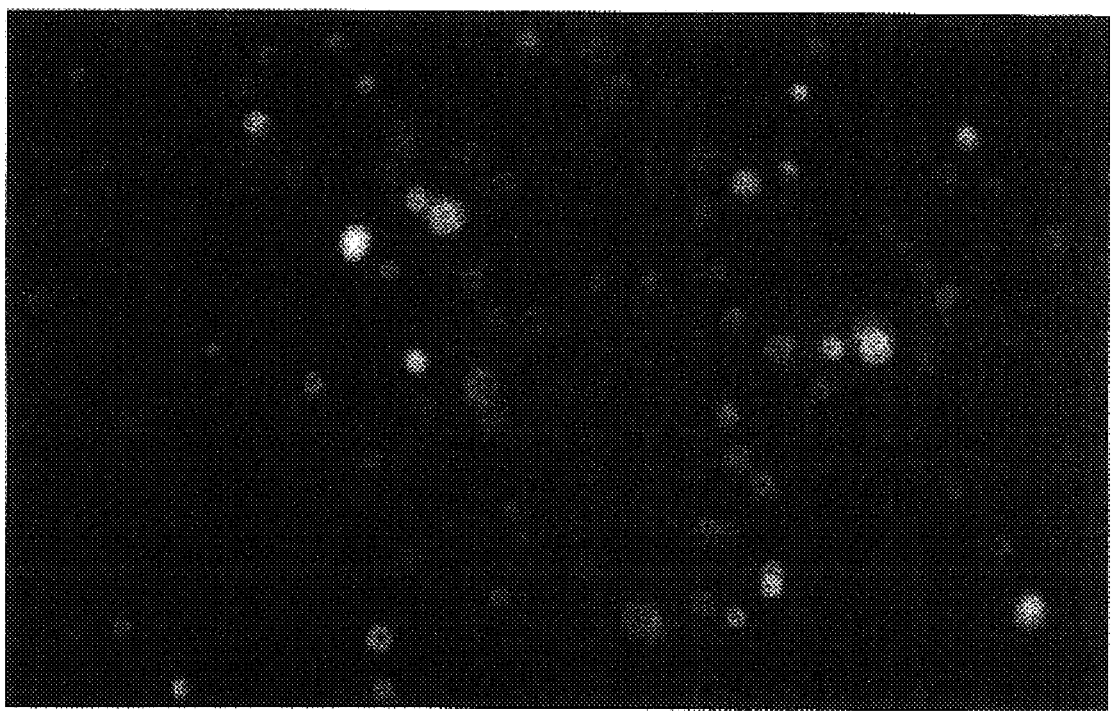
FIG. 5B shows M1619 melanoma cells treated with 5 µM disulfiram.
Figure 6A:
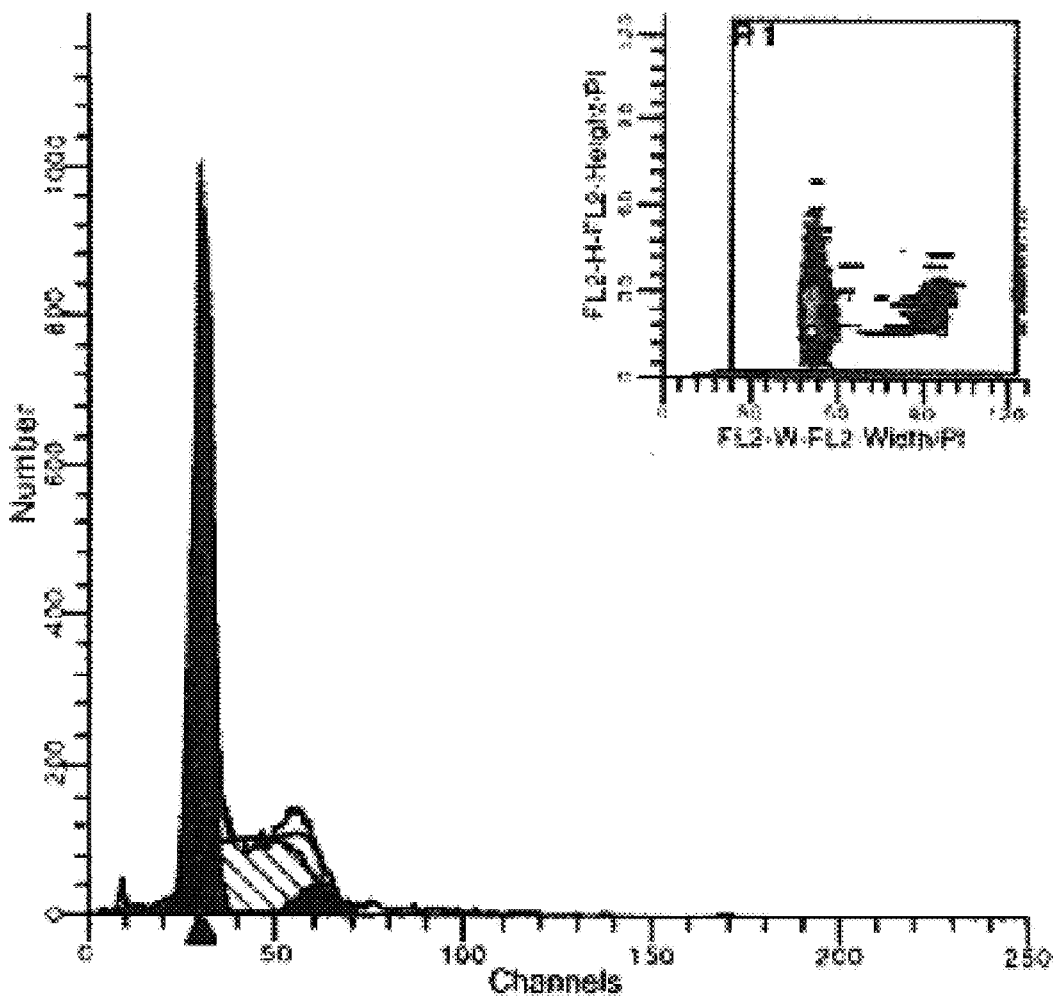
FIG. 6A shows that disulfiram combined with copper induces S-phase cell cycle arrest in M1619 melanoma cells and apopotosis.
Figure 6B:
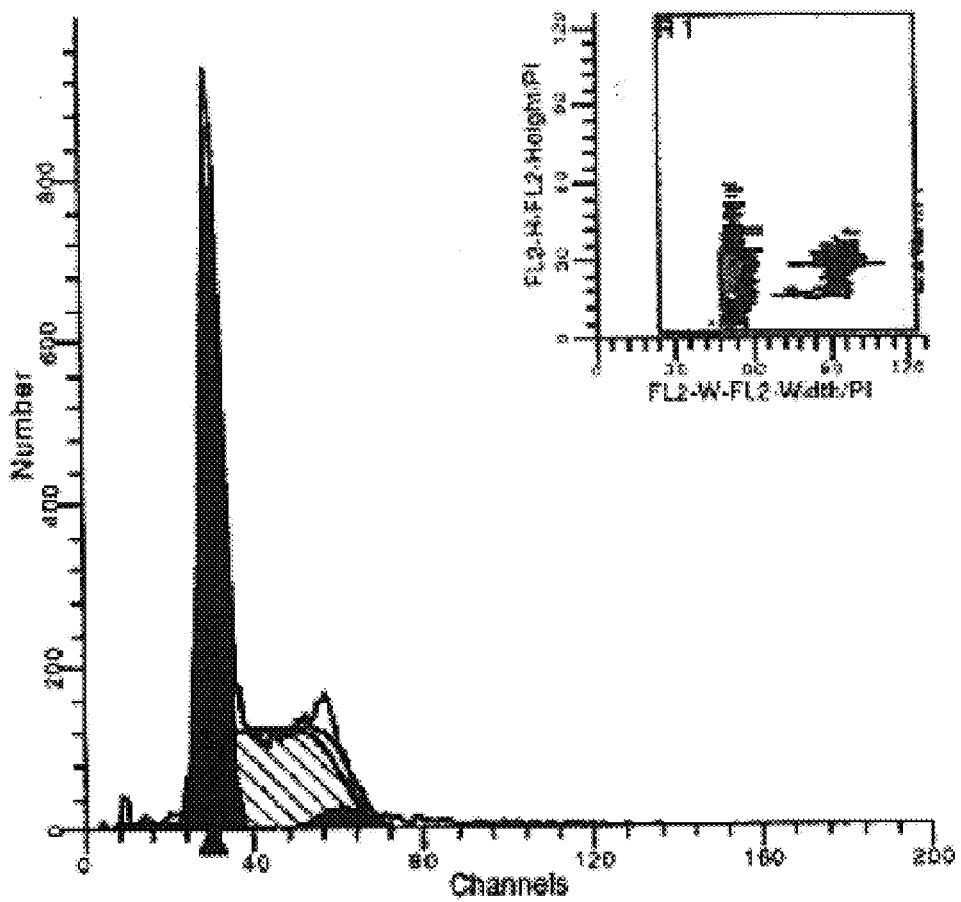
FIG. 6B shows that 5 µM disulfiram combined with copper induces S-phase cell cycle arrest in M1619 melanoma cells and apopotosis.
Figure 6C:
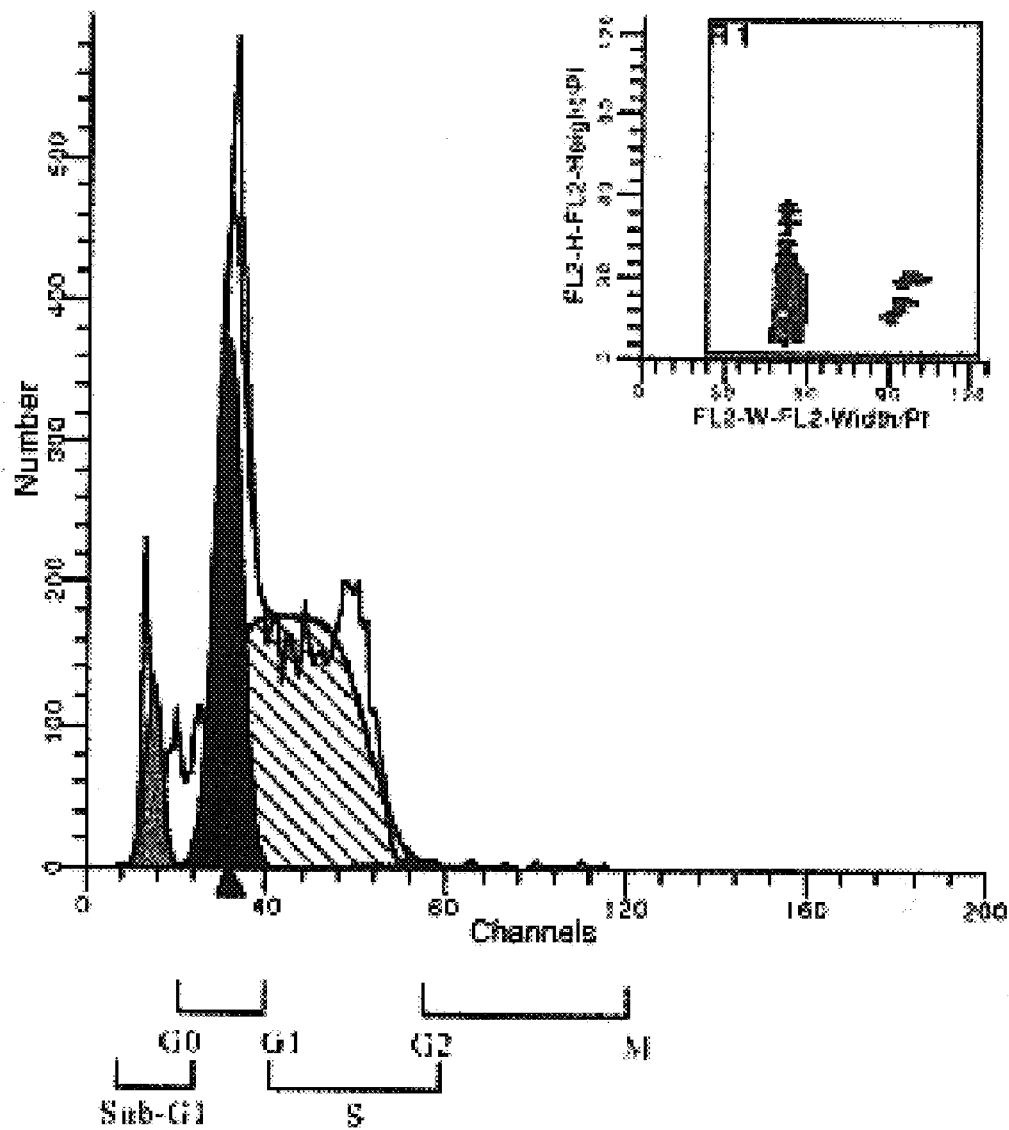
FIG. 6C shows that 5 µM disulfiram plus 250 µg/ml ceruloplasmin (Cerulo) as a source of copper.

In FIG. 5A, M1619 melanoma cells treated with DMSO vehicle. In FIG. 5B, M1619 melanoma cells treated with 5 $\mu$M disulfiram. Disulfiram markedly increases 3'-OH fluorescein end-labeling of DNA fragments. Cells were grown to confluence on 35 mm Petri dishes or on glass slides and treated for 15 hours with disulfiram or DMSO as vehicle. Apoptosis was studied by terminal deoxynucleotidyl transferase (TdT) dependent 3'-OH fluorescein end-labeling of DNA fragments, using a Fluorescein-FragEL™ DNA fragmentation detection kit (Oncogene Research Products, Cambridge, Mass.).

Table 2 shows that the combination of disulfiram and cisplatin or disulfiram and carmustine is significantly more antiproliferative against M1619 cells than cisplatin or carmustine alone:

TABLE 2

DISULFIRAM POTENTIATES THE ANTIPROLIFERATIVE ACTIVITY OF CHEMOTHERAPEUTIC AGENTS

| | A540 of MTT Formazan | |
|---|---|---|
| A. Cisplatin (ng/ml) | DMSO vehicle | Disulfiram 2.5 $\mu$M |
| 0 | 1.433 ± 0.038 | |
| 1 | 1.739 ± 0.041 | 1.369 ± 0.033[B] |
| 10 | 1.447 ± 0.047 | 1.221 ± 0.028 |
| 100 | 1.372 ± 0.052 | 1.183 ± 0.038[A] |
| 1,000 | 1.381 ± 0.098 | 0.921 ± 0.027[A] |
| B. Carmustine ($\mu$M) | DMSO vehicle | Disulfiram 0.6 $\mu$M |
| 0 | 0.104 ± 0.010 | |
| 1 | 0.197 ± 0.004 | 0.042 ± 0.003[C] |
| 10 | 0.152 ± 0.011 | 0.025 ± 0.002[C] |
| 100 | 0.020 ± 0.002 | 0.030 ± 0.023 |
| 1,000 | 0.003 ± 0.000 | 0.004 ± 0.000 |

In section A M1619 melanoma cells were cultured in 10% FBS and RPMI1640 at a density of 50,000 cells/well plates. After 48 hours cisplatin and 2.5 $\mu$M disulfiram or DMSO (5 $\mu$l per ml) were added to medium. After an additional 24 hours, proliferation was quantitated. Each bar represents mean MTT formazan absorbance in a minimum of 4 experiments. [A]p<0.05 compared to DMSO vehicle; [B]p<0.0 1 compared to DMSO vehcile.

In section B M1619 cells were cultured as above with addition of carmustine and 0.6 $\mu$M disulfiram or DMSO (5 $\mu$l per ml) to medium. After 24 hours, proliferation was quantitated. Each bar represents mean MTT formazan absorbance in a minimum of 4 experiments. [C]p<0.001 compared to DMSO vehicle.

Disulfiram was more potent as a growth inhibitor of neoplastic cell lines than its sulfhydryl-clontaining relative PDTC. As an example, the 50% inhibitor concentration ($IC_{50}$) against M1585 melanoma cells was approximately 1.25 $\mu$M for PDTC but was only 0.3 $\mu$M for disulfiram. This suggests that the active antiproliferative construct of thiocarbamates not likely the reduced thiol-containing monomeric form employed frequently as an antioxidant.

EXAMPLE 4

The antiproliferative activity of dithiocarbamate disulfides depends on complexation with copper. PDTC induces apoptosis in normal thymocytes that is mediated by complexation of copper from fetal bovine serum in the medium and subsequent facilitation of copper transport into cells. Because inhibition of CRE DNA-binding by disulfiram was shown to be copper dependent in FIGS. 1A–1C and FIG. 2, the growth inhibition of M1619 cells by disulfiram was studied to determine whether it was contingent on its ability to complex with metals present in growth medium. FIG. 4A shows that disulfiram combined with copper induces S-phase cell cycle arrest in M1619 melanoma cells and apopotosis. Unsynchronized M1619 melanoma cells were grown in the presence of DMSO vehicle (A), 5 $\mu$M disulfiram (B), or 5 $\mu$M disulfiram plus 250 $\mu$g/ml ceruloplasmin (Cerulo) as a source of copper (C). Twenty-four hours later, cells were harvested and flow cytometric analysis was performed. The proportion of nuclei in each phase of the cell cycle (brackets) was determined with MODFIT DNA analysis software. Disulfiram increases the portion of cells in S phase. The combination of disulfiram and ceruloplasmin further increases the number of cells in S phase, prevents progression into the $G_2$-M cell cycle and induces apoptosis.

Table 3 below shows that disulfiram greatly enhances intracellular uptake of copper, while FIG. 4B shows that the potent, cell impermeate $Cu^{2+}$ chelator bathocuproinie disulfonic acid (BCPS) greatly reduces growth inhibition from disulfiram. Conversely, the antiproliferative activity of disulfiram is greatly enhanced by supplementation of medium with concentrations of copper that do not by themselves affect cell growth (FIG. 4C). The copper transport protein ceruloplasmin, at levels normally present in human serum, can also serve as a source of copper that can be complexed to enhance the antiproliferative activity of disulfiram (FIG. 4D).

Disulfiram treatment of M1619 melanoma cultures (FIG. 4B) slightly reduces the number of cells in $G_0$–$G_1$ and increases the portion in S phase of the cell cycle. The addition of copper from ceruloplasmin to treatment with disulfiram greatly magnifies these effects. Over two-thirds of cells are in S phase, none are in $G_2$-M, and 6% are apoptotic as identified by flow cytometric cell cycle analysis (FIG. 4C). These studies suggest that growth inhibition of malignant cell lines by dithiocarbamates and their disulfides is not only dependent upon interaction with certain metal ions, but also from complexation with these metal ions and enhancing their intracellular transport.

TABLE 3

EFFECT OF DISULFIRAM ON INTRACELLULAR COPPER

| Treatment | Copper (ng/ml) |
| --- | --- |
| 10% FBS | 56 ± 7 |
| FBS + DMSO | 52 ± 4 |
| FBS + 0.625 µM DS | 76 ± 11 |
| FBS + 1.25 µM DS | 102 ± 5$^A$ |
| FBS + 2.5 µM DS | 160 ± 17$^A$ |
| FBS + 5.0 µM DS | 195 ± 3$^B$ |

M1619 melanoma cells were cultured at a density of 50,000 cells/well in 24 well plates in the presence of 10% FBS and grown to confluence. Disulfiram or DMSO vehicle (5 µl/ml) was added at the concentrations indicated, and cells were incubated an additional 6 hours. Supernatant was removed from cells and monolayers were washed twice with DPBS. Cells were scraped into 1.0 ml 3 N HCL/10% trichloroacetic acid and hydrolyzed at 70° C. for 16 hours. After centrifugation at 600 g×10 min, copper was measured using inductively coupled plasma emission spectroscopy at wavelengths of 324.754 and 224.700 nm. Replicates of four are reported. To minimize metal contamination, plastic ware rather than glass was used in experiments, and double-distilled, deionized water was used for all aqueous media. $^A$p<0.01 compared to DMSO control; $^B$p<0.001 compared to DMSO control.

EXAMPLE 5

This example shows dithiocarbate disulfides do not decrease proliferation through redox mechanisms.

Disulfirain failed to deplete GSH in M1619 cells (228+18 for FBS alone; 254+7 for DMSO vehicle control; 273±11 nmoles GSH/µg cell protein for 5 µM disulfiram), and the combination of 5.0 µM disulfiram and 1.6 µM $CuSO_4$ even increased intracellular GSH (293±16 nmoles GSH/µg cell protein; p<0.05 compared to FBS alone). Likewise, neither disulfiram (0.625 to 5 µM), $CuSO_4$ (0.2–1.6 µM) nor the combination of 1.25 µM disulfiram and 0.2 to 1.6 µM $CuSO_4$ caused measurable generation of reactive oxygen species in M1619 cells, measured using the $H_2O_2$-sensitive intracellular probe 2',7'-dichloroflurorescin. See, "J. A. Royall, et al., "Evaluation of 2',7'-dichlorofluorescin and dihydrorhodamine 123 as fluorescent probes for intracellular $H_2O_2$ in cultured endothelial cells," Archiv. Biochem. Biophys. 302:348–355 (1993). The baseline fluorescence of 1,431±23 units was not increased by any of the treatments.

In addition, the potent antioxidant probucol did not significantly inhibit growth of any of our tumor cell lines (data not shown). Augmentation of intracellular copper might also increase levels of the reactive nitrogen species nitric oxide (NO) through $Cu^{2+}$-mediated decomposition of S-nitrosoglutathione and other nitrosothiols (See, D. R. Arnelle, et al., "Diethyl dithiocarbamate-induced decomposition of S-nitrosothiols," Nitric Oxide. Biol. and Chem. 1:56–64 (1997); M. P. Gordge, et al., "Copper chelation-induced reduction of the biological activity of S-nitrosothiols," Brit. J. Pharmacol. 114:1083–1089 (1995); A. C. F. Gorren, et al., "Decomposition of S-nitrosoglutathione in the presence of copper ions and glutathione. Archiv. Biochem. Biophys," 330:219–2238 (1996)). NO, in turn, is believed to induce mitochondrial permeability transition and produce other effects, leading to apoptosis (See, S. B. Hortelano, et al., "Nitric oxide induces apoptosis via triggering mitochrondrial permeability transition. FEBS Lett," 410:373–377 (1997); Y. H. Shen, et al., "Nitric oxide induces and inhibits apoptosis through different pathways," FEBS Lett. 433:125–131 (1998)).

While the nitric oxide synthase inhibitor N6-nitro-L-arginine (LNAME) alone slightly enhanced cellular growth (23.7±2.3% increase; p<0.01 compared to DMSO vehicle control), LNAME did not eliminate the antiproliferative effect of disulfiram (36.8±4.0% inhibition by disulfiram alone vs 26.7±3.1% inhibition of growth in the presence of disulfiram plus LNAME; p<0.001 for each compared to DMSO vehicle control but not significantly different from each other). Finally, functioning as an antioxidant, PDTC has been postulated to interfere with growth of colorectal carcinoma in part by reducing expression of cyclooxygenase-2. See, r. Chinery, Nature Med, supra; R. Chinery, Cancer Res, supra. However, cyclooxygenase inhibitors failed to reduce growth in the cell lines we studied (data not shown). Thus, taken together, these data suggest that disulfiram does not appear to inhibit growth by adversely affecting the cellular redox state.

EXAMPLE 6

This example illustrates that metals other than copper can enhance the antiproliferaiive activity of dithiocarbamate disulfides. The absorption of copper at both the intestinal and cellular level is blocked by zinc cations, leading to the use of zinc acetate as the preferred treatment for Wilson's disease, the inherited disorder of copper overload.

Figure 7A:
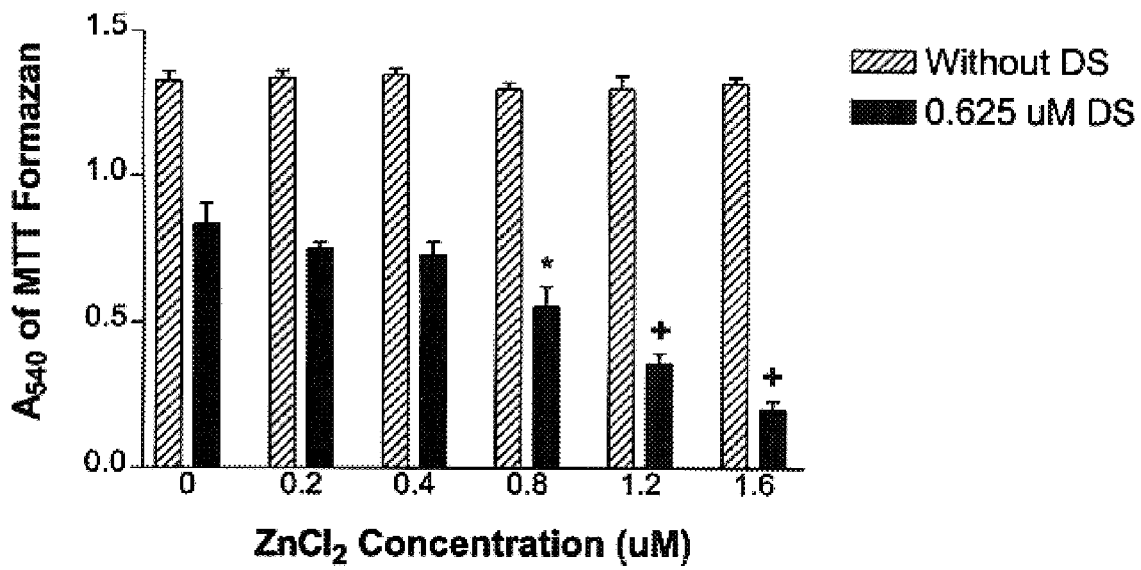
FIG. 7A shows that other metals also protentiate antiproliferative activity of disulfiram.

High zinc concentrations in culture media affect copper uptake and transport in differentiated human colon adenocarcinoma cells therefore it was determined whether zinc supplementation of medium could inhibit the antiproliferative activity of disulfiram, which appeared to be copper-dependent. Instead of reducing activity, zinc chloride also substantially enhanced the antiproliferative potential of disulfiram (FIG. 7A). Dithiocarbamates actively complex copper but can chelate other metals (See, R. P. Bums, et al., "1,1-dithiolato complexes of the transition elements," Adv. Inorg. Chem. Radiochem. 23:211–280 (1980)), raising the possibility that the activity of disulfiram might also be enhanced by supplementation with a variety of metal salts.

FIGS. 7A–7D show that other metals also protentiate antiproliferative activity of disulfiram. FIG. 7A shows that zinc potentiates the antiproliferative activity of disulfiram. M1619 cells were stimulated and plated as in FIG. 4. After 24 hours cells were treated, with indicated concentrations of zinc chloride ($ZnCl_2$) in the absence or presence of 0.625 µM disulfiram. After an additional 24 hr, cell number was quantitated. *p<0.01 compared to no $ZnCl_2$; +p<0.001 compared to no $ZnCl_2$.

Figure 7B:
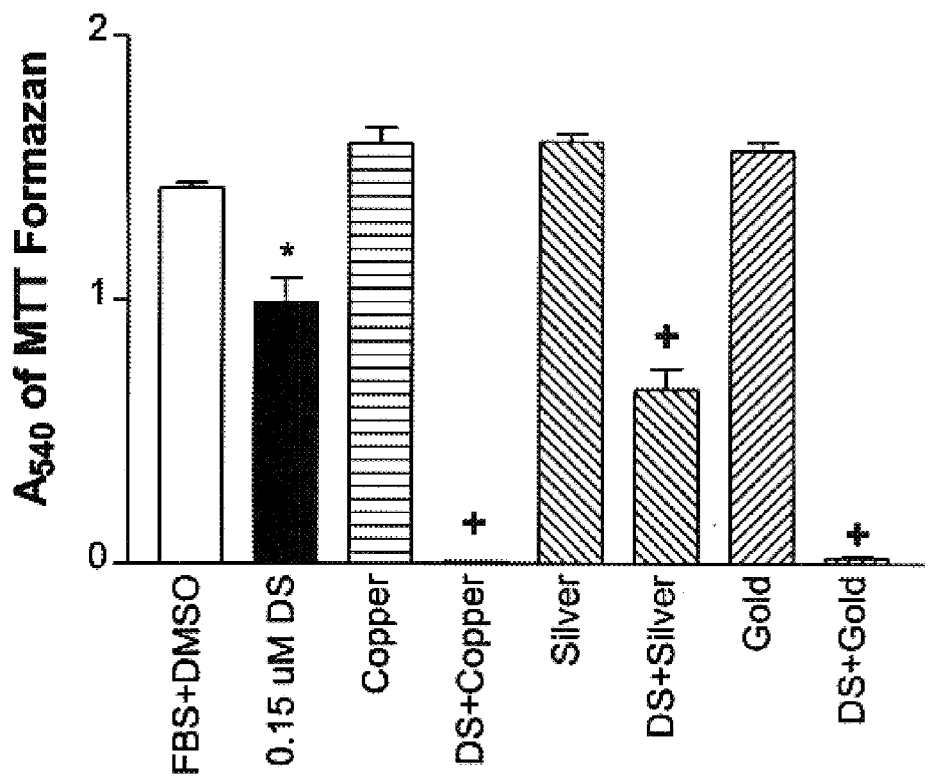
FIG. 7B shows the antiproliferative activity of disulfiram is enhanced by supplementation of medium with other heavy metals.

FIG. 7B shows that not only copper and zinc, but also salts of gold and silver can synergistically enhance the antiproliferative activity of disulfiram. This further supports the hypothesis that impairment of cellular proliferation by disulfiram and possibly other dithiocarbamates and their disulfides is dependent upon and enhanced catalytically by the presence of heavy metals. In FIG. 7B the antiproliferative activity of disulfiram is enhanced by supplementation of medium with other heavy metals. M1619 cells plated and stimulated as above were treated with FBS alone, DMSO vehicle (5 µl/ml), disulfiram (DS, 0.15 µM), 5 µM concentrations of metal salts (cupric sulfate, $CuSO_4$; silver lactate, $C_3H_5AgO_3$; gold chloride, $HAuCl_4 3H_2O$) or the combination of DS plus metal salts. After 48 hr cell number was quantitated. *p<0.05 compared to DMSO; +p<0.001 compared to DS alone.

Figure 7C:
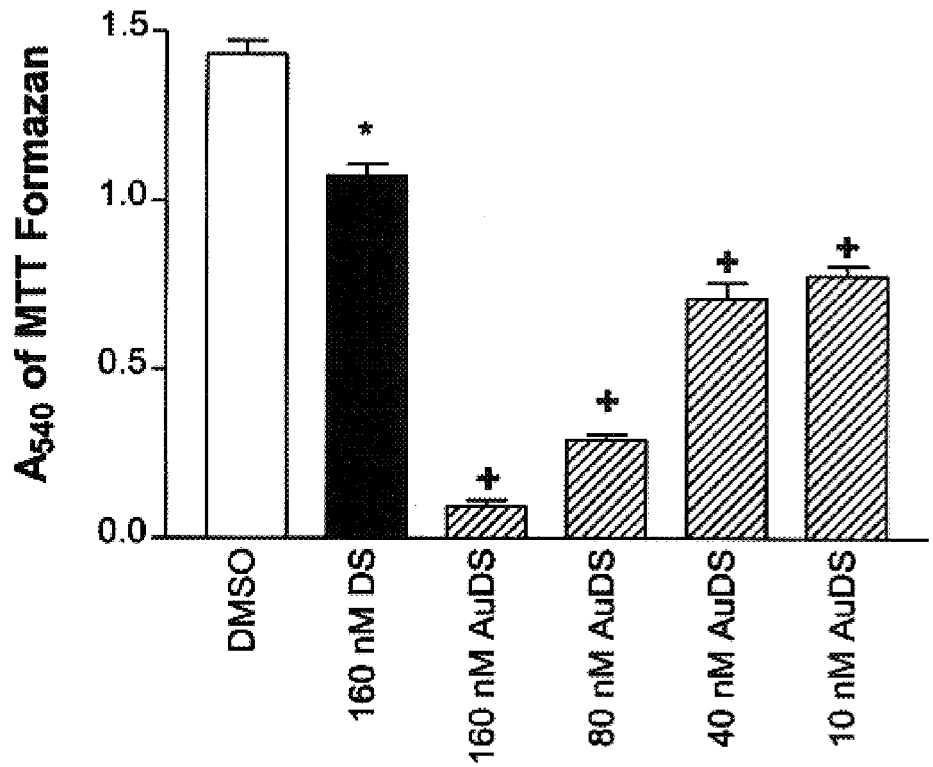
FIG. 7C shows complexes of disulfiram with gold demonstrate enhanced antiproliferative activity.

In FIG. 7C complexes of disulfiram with gold demonstrate enhanced antiproliferative activity. M1619 cells plated and stimulated as above were treated with FBS alone, DMSO vehicle (5 µl/ml), disulfiram (DS, 160 nM) or concentrations of gold complexed with disulfiram as outlined in Methods (AuDS). After 48 hr cell number was quantitated. *p<0.001 compared to DMSO; +p<0.001 compared to DS.

EXAMPLE 7

This example shows thiolate anion formation mediates the antiproliferative activity of dithiocarbamates and their disulfides.

In light of the above findings with metals, chelates of disulfiram with a number of metal ions, including $Cu^{2+}$, $Zn^{2+}$, $Ag^{1+}$, or $Au^{3+}$ were synthesized. During generation of disulfiram-metal complexes, chelation of metal ions from the aqueous phase was suggested by a color change in the disulfiram-containing chloroform phase (from pale yellow to brilliant golden orange with complexation of gold ions). All metal complexes showed increased antiproliferative activity compared to disulfiram, but the most active compound was formed by the complex of gold with disulfiram (FIG. 7C), which was antiproliferative at nM concentrations.

Figure 8:
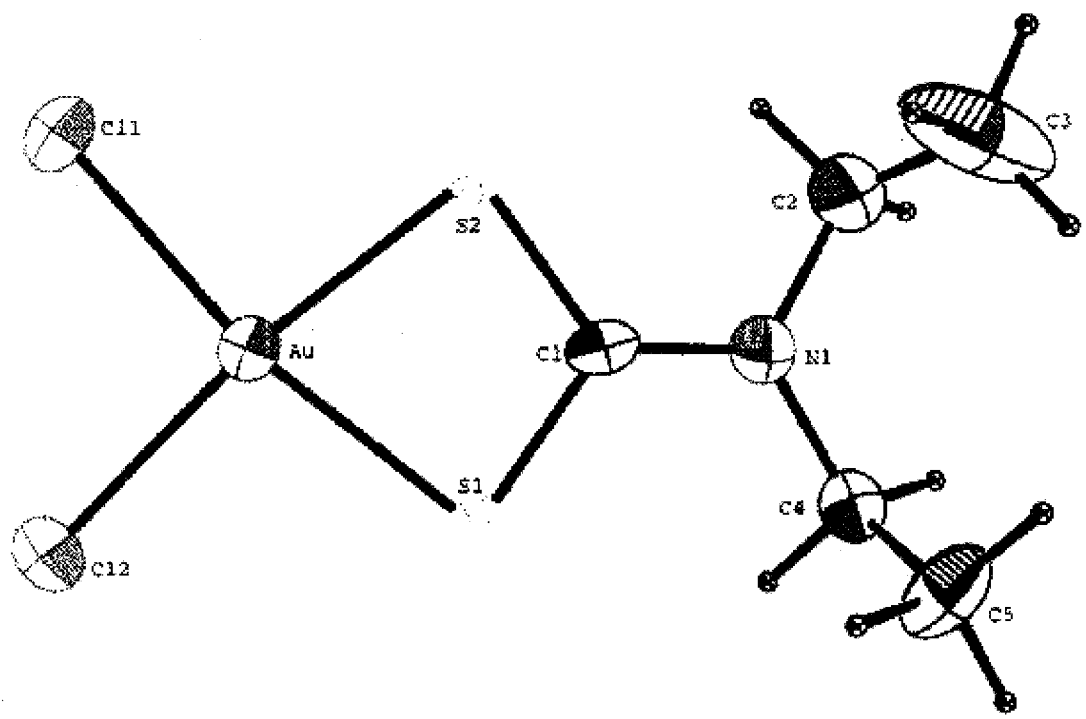
FIG. 8 shows the X-ray crystallographic structure of complexes formed from mixing gold tetrachloride and disulfiram.

The x-ray crystallographic structure of this compound revealed it to be a chelate of gold by the thiolate anion of diethyldithiocarbamate, with chlorides occupying the other two valences of gold (FIG. 8). Complexes were generated as outlined in Methods. Crystals were mounted on a Nonius Kappa-CCD diffractometer for evaluation. The crystal diffracted well and a data set was collected to 27.5° in θ using Mo Kα radiation (λ0.7173 A). Least-squares-refinement on the cell parameters reveled an orthorhombic P cell with unit cell parameters of a=11.5167(5), b=7.2472(2), c=12.9350(7) A, and a Volume of 1079.6(1) $A^3$. Examination of the systematic absences showed the space group to be Pnma. The structure was solved by direct methods using $SIR_{92}$ and revealed the crystal to be dichloro(diethylthiocarbamyl)gold (II). The structure was confirmed by the successful solution and refinement of the 83 independent variables for the 893 reflections (I>3δ(I)) to R-factors of 3.3 and 3.2%, with an ESD of 1.499. The gold complex is a square planar complex in which the Au and the four coordinated atoms sit on a mirror at x, 0.25, z. The organic ligand was found to be disordered with the diethylamine ligand occupying two sites related to each other through the mirror plane.

Figure 7D:
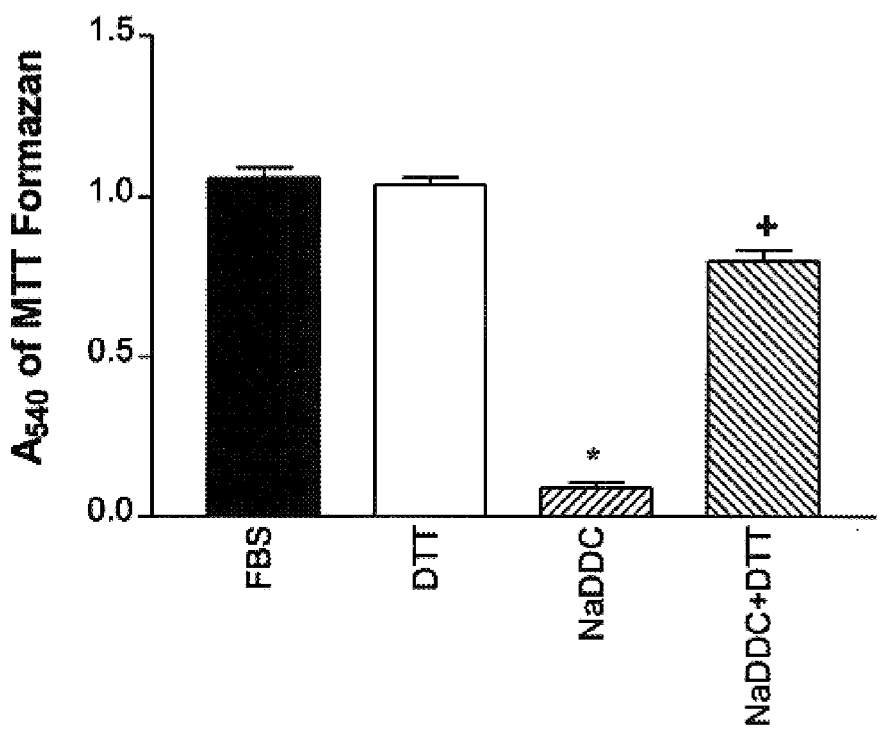
FIG. 7D shows the antiproliferative activity of the thiolate sodium diethyldithiocarbamate trihydrate (NaDDC) is reduced by low concentrations of DTT in the growth medium.

These results suggest that the proximate reactive dithiocarbamate structure important for promoting cellular mixed disulfide formation might be the thiolate anion generated from fully reduced dithiocarbamates or their disulfides by copper and other metals. To test this hypothesis the ability of the thiolate sodium diethyldithiocarbamate to inhibit M1619 proliferation alone or in the presence of a low concentration of DTT added to growth medium to promote formation of the fully reduced thioacid was compared. FIG. 7D shows that growth inhibition by the thiolate is greatly impaired by a concentration of DTT that does not affect growth of melanoma cells alone. In FIG. 7D the antiproliferative activity of the thiolate sodium diethyldithiocarbamate trihydrate (NaDDC) is reduced by low concentrations of DTT in the growth medium. M1619 cells plated and stimulated above were treated with FBS alone, NaDDC (1 µM), DTT (100 µM) or NaDDC plus DTT. After 48 hours cell number was quantitated. *p<0.001 compared to FBS; +p<0.001 compared to NaDDC alone. Thus, the function of metals in disrupting transcription factor DNA binding and cell proliferation may be to promote formation of the dithiocarbamate anion, the reactive chemical form that condenses into mixed disulfides with DNA binding region cysteines, with secondary conjugation to GSH, effecting transcription factor S-glutathionylation.

Many modification and other embodiments of the invention will come to mind to one skilled in the art to which this invention pertains, having the benefit of the teachings presented in the descriptions and the associated drawings contained herein. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed is:

1. A method of treating cancer in human cells sensitive to a dithiocarbamate thiolate anion of the formula set forth below and for sensitizing tumors to conventional cancer chemotherapy by blocking the P-glycoprotein membrane toxin extrusion pump and for sensitizing AIDS patients to anti-retroviral therapy by blocking the P-glycoprotein membrane toxin extrusion pump comprising administering to a human subject in need thereof a therapeutically effective amount of a dithiocarbamate thiolate anion of the formula:

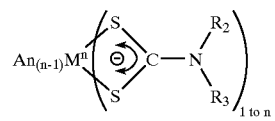

wherein $R_2$ and $R_3$ are the same or different and represent hydrogen, and unsubstituted or substituted alkyl, akenyl, aryl, and alkoxy groups; M is an alkali metal selected from the group consisting of sodium, potassium, calcium, magnesium, barium, and lithium; An is copper; n is the valence of the metal.

2. The method according to claim 1 wherein said dithiocarbamate thiolate anion is in the form of a pharmaceutically acceptable salt.

3. The method according to claim 1 wherein said dithiocarbamate thiolate anion is administered in a dosage of between about 125 to about 1000 mg per day of body weight.

4. The method according to claim 1 wherein said dithiocarbamate thiolate anion is administered in a dosage of between about 250 to about 500 mg per day.

5. The method according to claim 1 wherein said dithiocarbamate thiolate anion is administered parenterally.

6. The method according to claim 1 wherein said dithiocarbamate thiolate anion is administered orally.

7. The method according to claim 1 wherein said cancer is melanoma, lung cancer, renal cancer, colorectal cancer, breast cancer, pancreatic cancer, gastric cancer, bladder cancer, ovarian cancer, uterine cancer, lymphoma, and prostrate cancer.

8. The method according to claim 1 wherein said alkyl, akenyl, aryl and alkoxy groups are substituted.

9. The method according to claim 1 wherein said aryl group is a heteroaryl.

* * * * *